(12) United States Patent
Ansari et al.

(10) Patent No.: US 10,821,296 B2
(45) Date of Patent: Nov. 3, 2020

(54) SYSTEMS AND METHODS FOR THE AUTOMATED DELIVERY OF PHOTOBIOMODULATION THERAPY TO A PATIENT

(71) Applicants: Nadia Ansari, Tustin, CA (US); Kamran Ansari, Tustin, CA (US)

(72) Inventors: Nadia Ansari, Tustin, CA (US); Kamran Ansari, Tustin, CA (US)

(*) Notice: Subject to any disclaimer, the term of this patent is extended or adjusted under 35 U.S.C. 154(b) by 0 days.

(21) Appl. No.: 16/586,250

(22) Filed: Sep. 27, 2019

(65) Prior Publication Data

US 2020/0222713 A1    Jul. 16, 2020

Related U.S. Application Data

(63) Continuation of application No. 16/248,692, filed on Jan. 15, 2019, now Pat. No. 10,463,874.

(51) Int. Cl.
*A61B 18/18* (2006.01)
*A61N 5/06* (2006.01)
*A61N 5/067* (2006.01)

(52) U.S. Cl.
CPC ...... *A61N 5/0613* (2013.01); *A61N 2005/067* (2013.01); *A61N 2005/0626* (2013.01); *A61N 2005/0633* (2013.01); *A61N 2005/0642* (2013.01); *A61N 2005/0644* (2013.01); *A61N 2005/0645* (2013.01); *A61N 2005/0666* (2013.01)

(58) Field of Classification Search
CPC ...... A61N 2005/0626; A61N 2005/067; A61N 5/0613; A61N 2005/0642; A61N 2005/0644; A61N 2005/0645; A61N 2005/0666; A61N 2005/0633
See application file for complete search history.

(56) References Cited

U.S. PATENT DOCUMENTS 6,942,658 B1    9/2005  Rizoiu
2010/0016783 A1*  1/2010  Bourke, Jr. ............ A61N 5/10
                                                          604/20

OTHER PUBLICATIONS

What is LLLT / Photobiomodulation Therapy? THOR Photomedicine Ltd, Internet Citation, 2019, pp. 1-3; URL: https://www.thorlaser.com/LLLT/; Retrieved from Internet Feb. 26, 2019.
THOR Product Brochure White, THOR Photomedicine Ltd, 2019, pp. 1-2; Retrieved Jan. 14, 2019; URL:https://www.thorlaser.com/downloads/brochure/THOR-Brochure_White_v1.1.pdf.
THOR Product Brochure Black, THOR Photomedicine Ltd, 2019, pp. 1-4; Retrieved Jan. 14, 2019; URL: https://www.thorlaser.com/downloads/brochures/THOR-Brochure-web.pdf.

(Continued)

*Primary Examiner* — Alyssa M Alter
(74) *Attorney, Agent, or Firm* — Novel IP

(57) ABSTRACT

Systems and methods for treating neuropathic pain by using a photobiomodulation device in a handheld manner. A robotic arm is attached to a light emitting device and controlled, using a visual display, to automatically position the light emitting device over areas to be treated on the patient's body. The automated light delivery process allows a patient to treat large portions of her body in a handsfree manner.

20 Claims, 18 Drawing Sheets

(56) References Cited

OTHER PUBLICATIONS

James D Carroll "Introduction to Low Level Light Therapy (LLLT) for pain relief", THOR Photomedicine Ltd (UK), www.thorlaser.com, pp. 1-19; Retrieved Jan. 14, 2019; https://www.thorlaser.com/downloads/research/THOR-LLLT-Pain-research.pdf.

Sport THOR Photomedicine System, Low Level Laser Therapy for the Rapid Recovery of Sports Injuries; www.thorlaser.com, pp. 1-16; Retrieved Jan. 14, 2019; URL: https://www.thorlaser.com/downloads/research/THOR-LLLT-soft-tissue-research.pdf.

James Carroll "Wound Healing", Photobiomodulation (PBM) / Low Level laser Therapy (LLLT), THOR Photomedicine Research Digest, www.thorlaser.com, May 4, 2018, 10 pages, THOR Photomedicine Ltd 2018, URL: https://www.thorlaser.com/downloads/research/THOR-LLLT-wound-healing-research.pdf.

How Laser Therapy works/"Dosage" is a difficult subject. Why?, THOR Photomedicine Ltd, Internet Citation, 2019, pp. 1-8; URL: https://www.thorlaser.com/Dosage.htm; Retrieved from Internet Feb. 26, 2019.

Huang et al. "Biphasic Dose Response in Low Level Light Therapy", International Dose-Response Society, Dose-Response (Prepress), Formerly Nonlinearity in Biology, Toxicology and Medicine, 2009, Unitversity of Massachusetts, 26 pages, ISSN: 1559-3258, DOI: 10.2203/dose-response.09-027.Hamblin.

Dr. Partricia Burton "A selection of recent papers demonstrating cognition—and mood enhancing effects of PBMT", Photobiomodulation (PBM) / Low Level laser Therapy (LLLT), THOR Photomedicine Research Digest, www.thorlaser.com, Aug. 3, 2018, prepared for THOR website, 8 pages, THOR Photomedicine Ltd 2018, URL: https://www.thorlaser.com/downloads/research/Cognition-and-Mood-research.pdf.

Joint Conditions Research, THOR Photomedicine Research Digest, www.thorlaser.com, Retrieved Jan. 14, 2019, prepared for THOR website, 113 pages, THOR Photomedicine Ltd 2019; URL: https://www.thorlaser.com/downloads/research/Joint-conditions-THOR-Research-Digest.pdf.

Dr. Partricia Burton "Lymphoedema lymphedema", Photobiomodulation (PBM) / Low Level laser Therapy (LLLT), THOR Photomedicine Research Digest, www.thorlaser.com, Feb. 11, 2019, prepared for THOR website, 33 pages, THOR Photomedicine Ltd 2019, URL: https://www.thorlaser.com/downloads/research/Lymphoedema-lymphedema-THOR-Research-Digest.pdf.

Dr. Partricia Burton "A selection of papers around PBMT and exercise, highlighting delayed onset muscle soreness (DOMS), fatigue, slowing of age-related muscle loss and an interesting look at epigenetics with evidence of upregulation of oxidative stress defence mechanisms.", Photobiomodulation (PBM) / Low Level laser Therapy (LLLT), THOR Photomedicine Research Digest, www.thorlaser.com, Aug. 28, 2018, prepared for THOR website, 8 pages, THOR Photomedicine Ltd 2018; URL: https://www.thorlaser.com/downloads/research/Muscle-fatigue-endurance-strength-and-recovery-THOR-Research-Digest.pdf.

Radiation Dermatitis Research, THOR Photomedicine Research Digest, www.thorlaser.com, Retrieved Jan. 14, 2019, prepared for THOR website, 10 pages, THOR Photomedicine Ltd 2019, URL: https://www.thorlaser.com/downloads/research/Radiation-Dermatitis-THOR-Research-Digest.pdf.

James D Carroll "for tendinopathies", Research Digest, Low Level laser Therapy (LLLT) / Photobiomodulation (PBM), THOR Photomedicine Research Digest, www.thorlaser.com, 113 pages, THOR Photomedicine Ltd (UK) 2016, URL: https://www.thorlaser.com/downloads/research/Tendinopathies-THOR-Research-Digest.pdf.

Office Action dated Jun. 13, 2019 for U.S. Appl. No. 16/248,692.

* cited by examiner

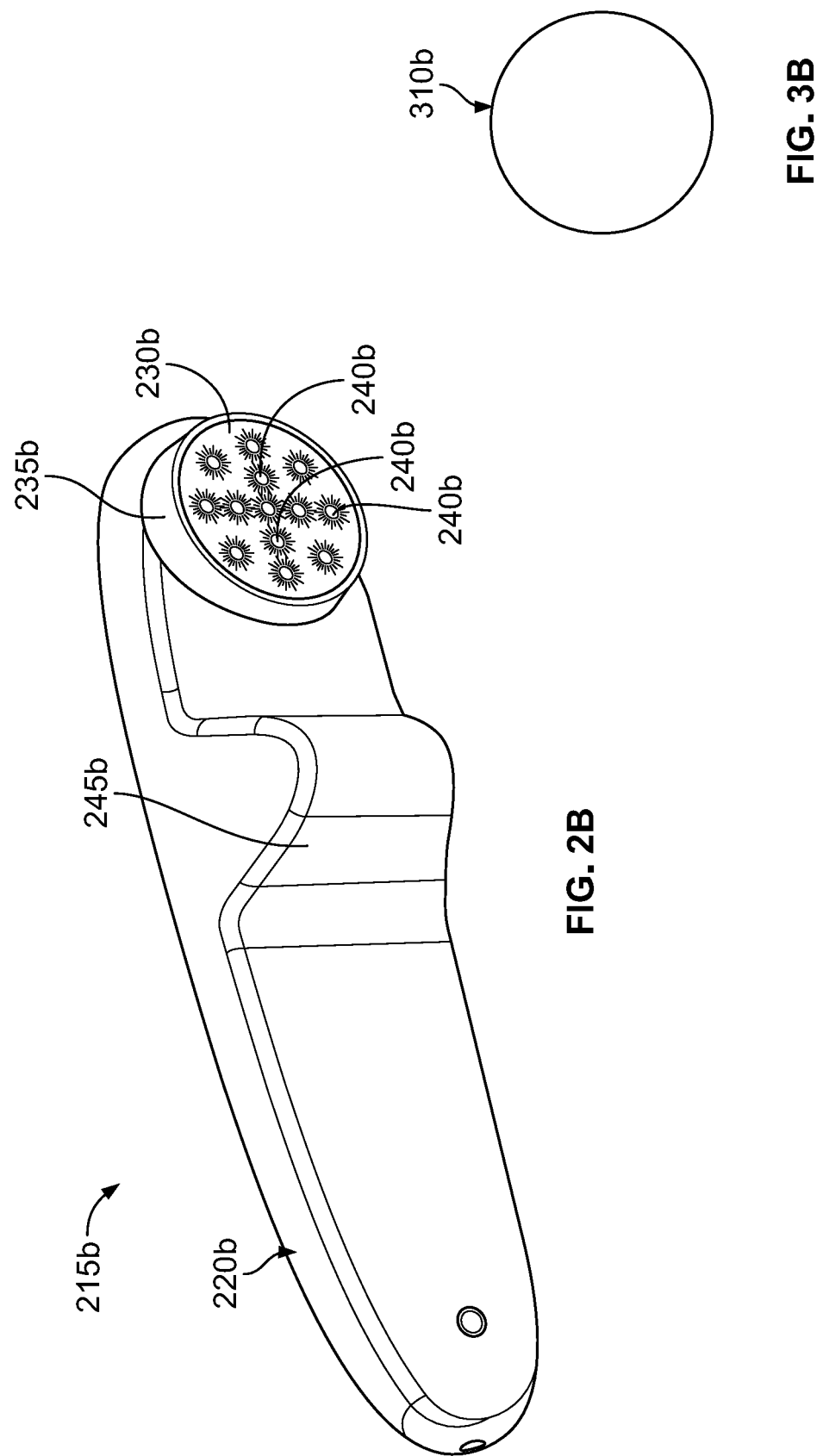

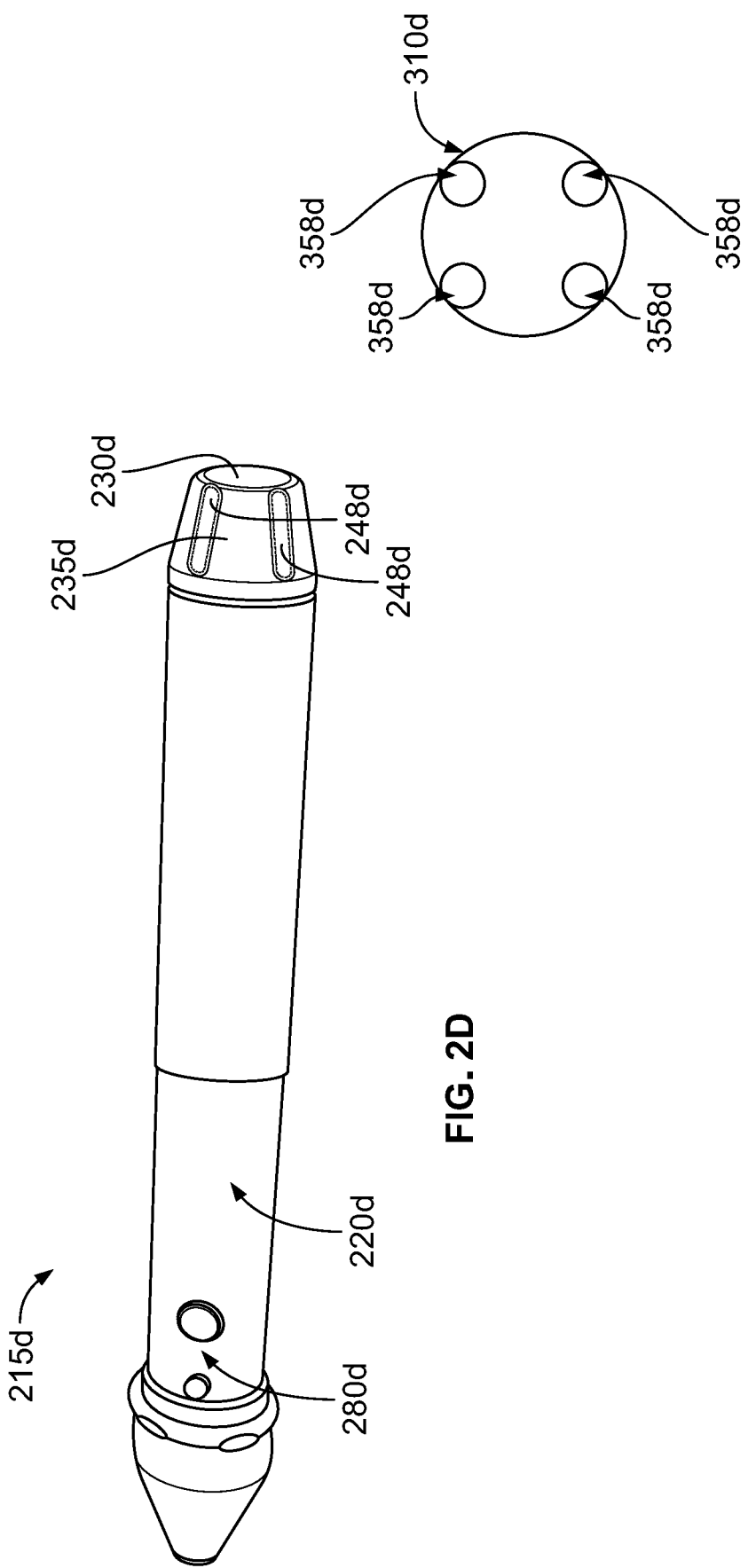

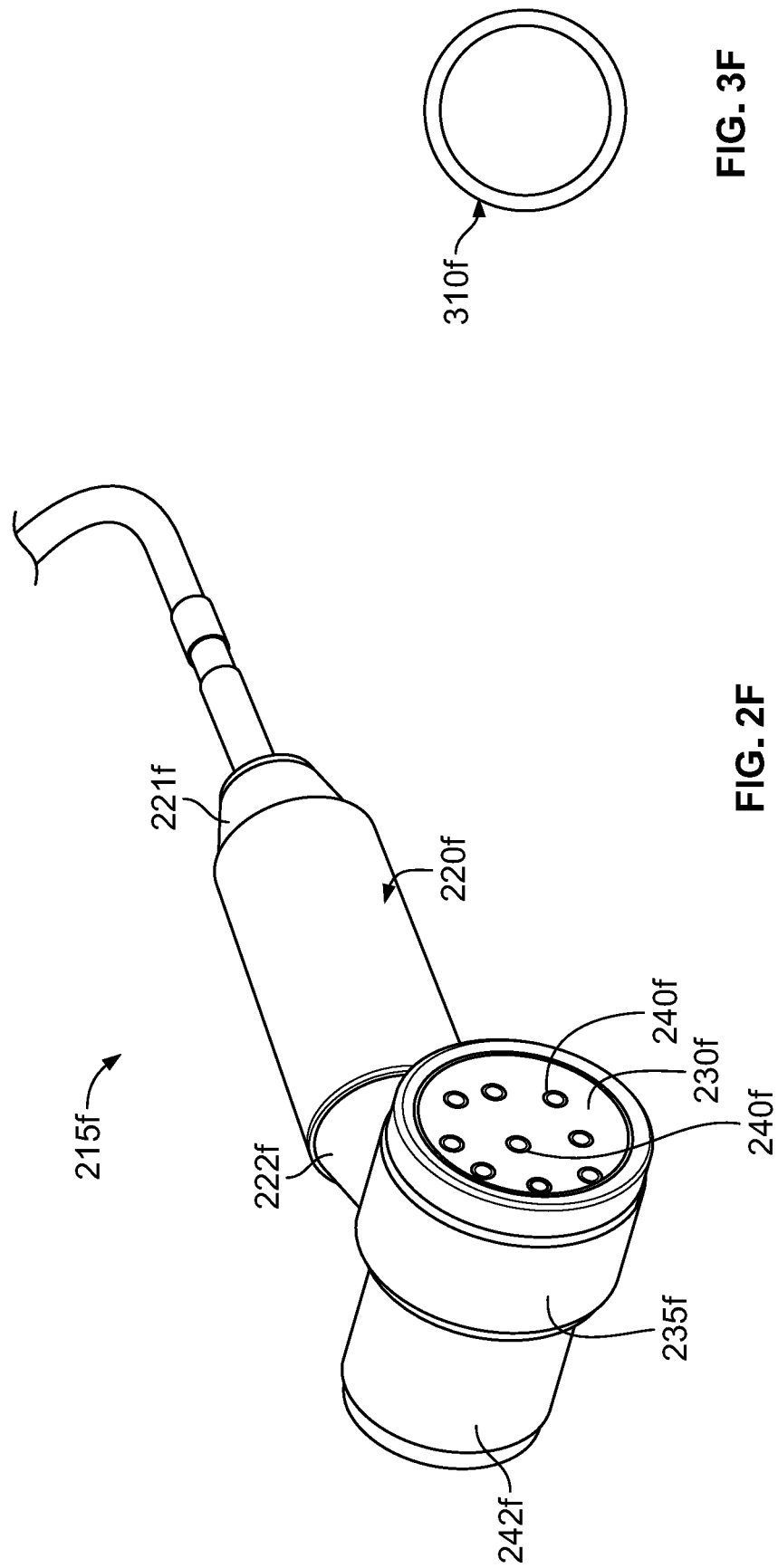

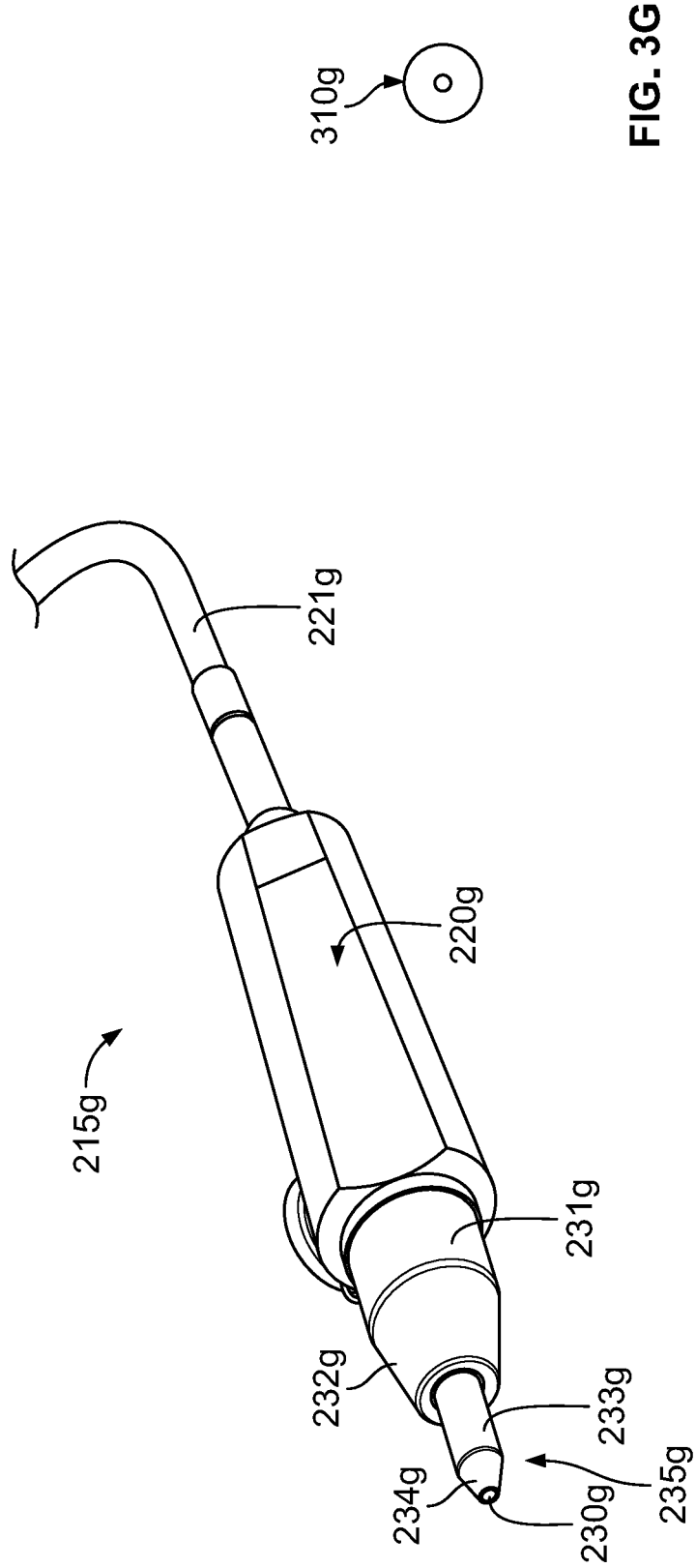

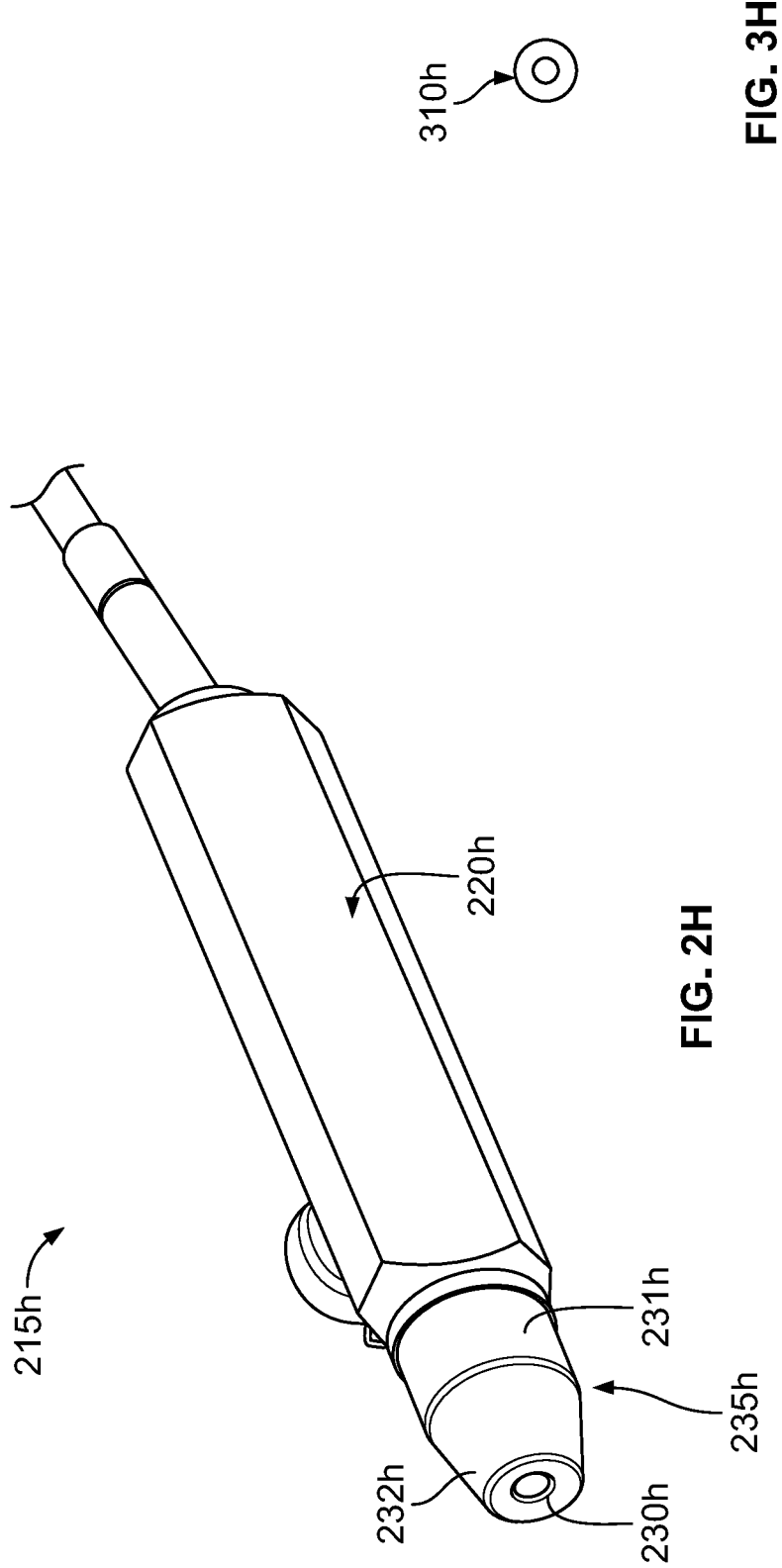

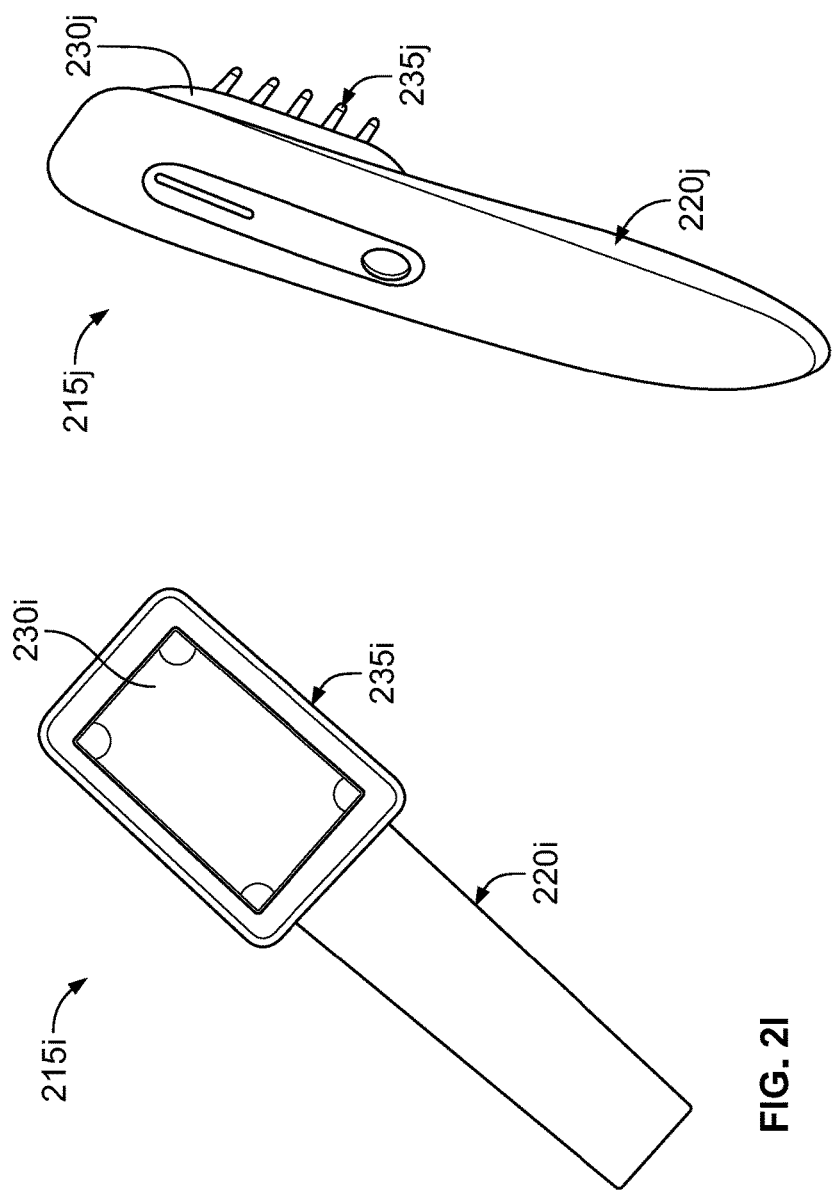

SYSTEMS AND METHODS FOR THE AUTOMATED DELIVERY OF PHOTOBIOMODULATION THERAPY TO A PATIENT

CROSS-REFERENCE

The present application is a continuation application of U.S. patent application Ser. No. 16/248,692, entitled "Systems and Methods for Providing Cold Laser Therapy to a Patient in a Hands-Free Manner" and filed on Jan. 15, 2019, and is therefore entitled to the filing date thereof. U.S. patent application Ser. No. 16/248,692 is hereby incorporated by reference into this application in its entirety.

FIELD OF THE INVENTION

The present application relates generally to holder and positioning devices to enable an effective delivery of cold laser therapy and, more specifically, to devices capable of being secured to a patient's skin and of removably receiving, and holding in place, a cold laser wand so that a patient may use the device in a hands-free manner.

BACKGROUND

Cold laser devices are low-intensity laser systems, typically comprising a hand-held wand and a generator either separate or integrated into a single housing, that generate low levels of light. Exposing a patient's skin to low levels of light achieves numerous health benefits. During this conventional procedure, the handheld wand of a cold laser device is positioned proximate the patient's skin and different wavelengths and outputs of low-level light are applied directly to a targeted area. When the patient's tissue absorbs the light, red and near-infrared light cause a reaction, damaged cells respond with a physiological reaction that promotes regeneration, and healing occurs. Skin tissue is commonly treated with wavelengths between 600 and 700 nanometers (nm) and, for deeper penetration, with wavelengths between 780 and 950 nm. These devices are also referred to as low-level laser therapy, low-power laser therapy, soft laser biostimulation, and photobiomodulation, collectively referred to as cold laser therapy devices.

While potentially therapeutically effective, existing cold laser systems with handheld wands require a therapist or patient to hold the device at a particular range from the area of skin requiring treatment for many minutes at a time. For example, the handheld wand may be required to be held just above a treatment site for anywhere from 15 seconds to 1 hour. Therapists and patients find it difficult to hold the device in place for such long periods of time. This problem is particularly exacerbated in patients with severe pain or chronic neuropathy, in situations where the device needs to be proximate to the skin, but not touching the skin due to pain, and in situations where the patient is attempting to self-treat but the location of the pain is difficult to reach.

It is therefore desirable to have a system for transforming a conventionally handheld treatment method into a hands-free treatment method. It is further desirable to have a way of securing a cold laser wand to any portion of the patient's body, thereby enabling hands-free treatment in difficult to reach locations. It is further desirable to have a securing system that can accommodate different size wands to enable a clinician to use different therapeutic modalities. It is also desirable to have a securing system that can adjust the distance of the wand head from the patient's skin to allow for a range of different exposure distances and to better capture and direct light from a device to the patient's skin. Additionally, because many chronic neuropathy patients suffer from sensitivity to touch (allodynia), it would be beneficial to have a system that would alter the distance of the device from the patient's skin while not unduly exposing the patient's skin to abrasive or undesirable materials.

SUMMARY OF THE INVENTION

The present specification discloses a method of treating peripheral neuropathic pain using a handheld cold laser device comprising: acquiring the handheld cold laser device, wherein the handheld cold laser device comprises a light emission surface and a body attached to, but separate from, the light emission surface; attaching a patient attachment surface to a portion of a patient's body, wherein the patient attachment surface comprises a light emission surface receiver; attaching the light emission surface to the light emission surface receiver, wherein the light emission surface receiver comprises a hollow cavity enclosed by a first wall, wherein the first wall has a periphery, and wherein an external surface of the light emission surface is positioned inside the periphery; adjusting a position of a support member having a first end and a second end, wherein the first end of the support member is attached to at least one of the light emission surface receiver or the patient attachment surface, wherein the second end of the support member is in physical contact with the body of the handheld cold laser device, and wherein the second end of the support member is adjusted such that the light emission surface is maintained in a position parallel to the patient's skin in a hands-free manner; and activating the handheld cold laser device to transmit light from the light emission surface through the light emission surface receiver and to the patient's body.

Optionally, the method further comprises adjusting the periphery of the light emission surface receiver to achieve a friction fit with the external surface of the light emission surface.

Optionally, adjusting the position of the support member comprises rotating the support member, wherein the support member is hinged at one end to at least one of the light emission surface receiver or the patient attachment surface. Optionally, the support member comprises a curved portion at a second end to receive the body of the cold laser device.

Optionally, an internal surface of the first wall comprises a reflective material wherein the reflective material is positioned to cause light emitted from the light emission surface and impinging on the internal surface of the first wall to be directed toward the patient's skin. Optionally, at least 20% of the internal surface of the first wall comprises the reflective material. Optionally, at least 50% of the internal surface of the first wall comprises the reflective material. Optionally, at least 70% of the internal surface of the first wall comprises the reflective material.

Optionally, the wall of the light emission surface receiver has a plurality of holes to release heat generated from light emitted by the light emission surface.

Optionally, the wall of the light emission surface is porous.

Optionally, the wall of the light emission surface receiver is vertically adjustable to thereby modify a distance between the light emission surface and the patient's skin.

Optionally, the light emission surface receiver is detachable from the patient attachment surface.

Optionally, the light emission surface receiver is attached to the patient attachment surface using at least one of a friction fit, Velcro, snaps, a sewed connection, or glue.

Optionally, the support member comprises a height adjustment mechanism and adjusting the position of the support member comprises modifying the height adjustment mechanism.

Optionally, the support member comprises a telescopic height adjustment mechanism and adjusting the position of the support member comprises turning a dial to cause one portion of the support member to move relative to a second portion of the support member.

Optionally, the light emission surface receiver comprises a second wall that encloses the first wall, wherein an interior surface of the second wall is attached to an exterior surface of the first wall through a member and wherein the second wall is configured to permit heat to flow away from the patient's body. Optionally, the first wall has a first length and the second wall has a second length, wherein the first length is less than the second length, and wherein the second wall comprises a plurality of openings.

Optionally, the method further comprises deactivating the handheld cold laser device to turn off light from the light emission surface after a period of time, wherein the period of time is sufficient to at least partially treat the peripheral neuropathic pain.

Optionally, the light emission surface has a first geometric shape and the light emission receiver has a second geometric shape, wherein the second geometric shape is similar to the first geometric shape but of a different size. Optionally, the first geometric shape is at least one of rectangular, circular, oval, trapezoidal, triangular, polygonal, or conical.

The aforementioned and other embodiments of the present specification shall be described in greater depth in the drawings and detailed description provided below.

BRIEF DESCRIPTION OF THE DRAWINGS

These and other features and advantages of the present specification will be further appreciated, as they become better understood by reference to the following detailed description when considered in connection with the accompanying drawings:

FIG. 2B illustrates a second embodiment of a wand with light emission surfaces of a second shape and a second size, in accordance with the present specification;

FIG. 2D illustrates a fourth embodiment of a wand with light emission surfaces of a fourth shape and a fourth size, in accordance with the present specification;

FIG. 2F illustrates a sixth embodiment of a wand with light emission surfaces of a sixth shape and a sixth size, in accordance with the present specification;

FIG. 2G illustrates a seventh embodiment of a wand with light emission surfaces of a seventh shape and a seventh size, in accordance with the present specification;

FIG. 2H illustrates an eighth embodiment of a wand with light emission surfaces of an eighth shape and an eighth size, in accordance with the present specification;

FIG. 2I illustrates a ninth embodiment of a wand with light emission surfaces of a ninth shape and a ninth size, in accordance with the present specification;

FIG. 2J illustrates a tenth embodiment of a wand with light emission surfaces of a tenth shape and a tenth size, in accordance with the present specification;

FIG. 3B illustrates a top view of a second embodiment of a light emission receiver, incorporated into a patient attachment system, of a second shape and second size that corresponds to the embodiment illustrated in FIG. 2B;

FIG. 3D illustrates a top view of a fourth embodiment of a light emission receiver, incorporated into a patient attachment system, of a fourth shape and fourth size that corresponds to the embodiment illustrated in FIG. 2D;

FIG. 3F illustrates a top view of a sixth embodiment of a light emission receiver, incorporated into a patient attachment system, of a sixth shape and sixth size that corresponds to the embodiment illustrated in FIG. 2F;

FIG. 3G illustrates a top view of a seventh embodiment of a light emission receiver, incorporated into a patient attachment system, of a seventh shape and seventh size that corresponds to the embodiment illustrated in FIG. 2G;

FIG. 3H illustrates a top view of an eighth embodiment of a light emission receiver, incorporated into a patient attachment system, of an eighth shape and eighth size that corresponds to the embodiment illustrated in FIG. 2H;

FIG. 3I illustrates a top view of a ninth embodiment of a light emission receiver, incorporated into a patient attachment system, of a ninth shape and ninth size that corresponds to the embodiment illustrated in FIG. 2I;

FIG. 3J illustrates a top view of a tenth embodiment of a light emission receiver, incorporated into a patient attachment system, of a tenth shape and tenth size that corresponds to the embodiment illustrated in FIG. 2J;

DETAILED DESCRIPTION

Figure 1:
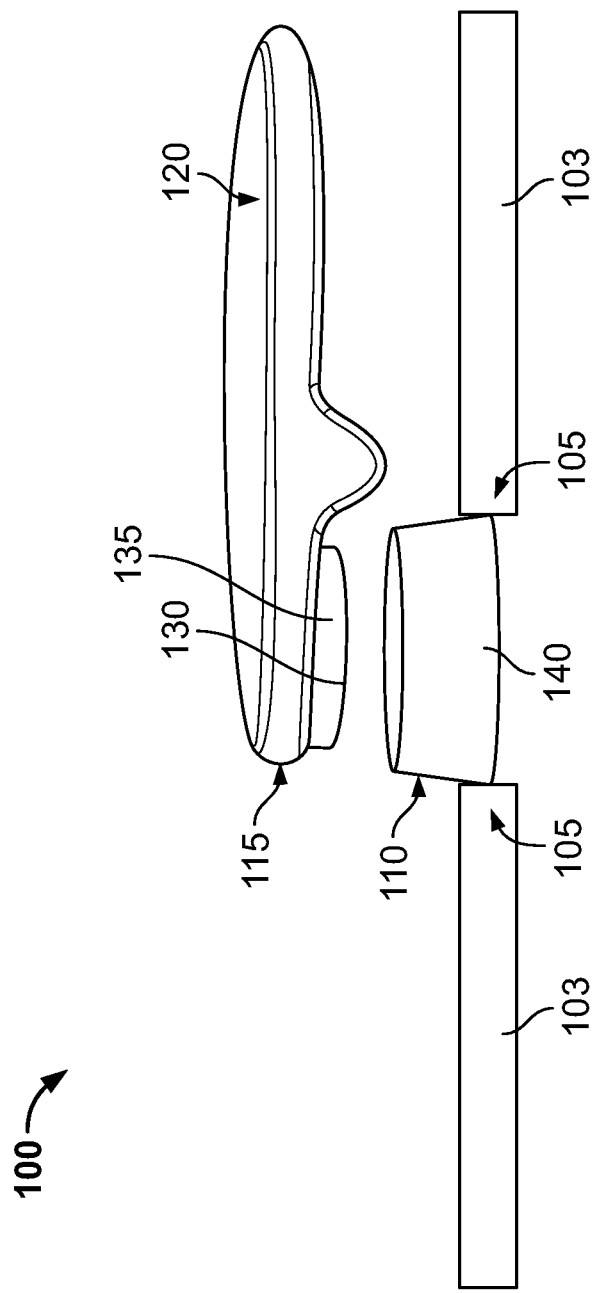
FIG. 1 illustrates an exemplary handheld wand and attachment system in accordance with some embodiments of the present specification.

The present invention may be used to treat, in a substantially hands-free manner, numerous conditions, including ligament sprains, muscle strains, tendonitis, bursitis, neck pain, back pain, knee pain, muscle spasms, inflammation, swelling, ulcerations, rheumatoid arthritis, autoimmune diseases, peripheral neuropathy, fibromyalgia, carpal tunnel syndrome, acne, psoriasis, burns, vitiligo, edema, dermatitis, rashes, wounds related to diabetes, and diabetic neuropathy.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

In the description and claims of the application, each of the words "comprise" "include" and "have", and forms thereof, are not necessarily limited to members in a list with which the words may be associated. It should be noted herein that any feature or component described in association with a specific embodiment may be used and implemented with any other embodiment unless clearly indicated otherwise.

As used herein, the indefinite articles "a" and "an" mean "at least one" or "one or more" unless the context clearly dictates otherwise.

As used herein, the term "cold laser wand" refers to a handheld device that emits light, and preferably one or more beams of coherent monochromatic light by the stimulated emission of photons from excited atoms, with wavelengths between 600 and 950 nanometers (nm).

As used herein, the term "hands-free manner" refers to the positioning and use of a cold laser device such that the preferred positioning of the device is maintained without requiring a person to hold the device.

While potentially therapeutically effective, existing cold laser systems with handheld wands require a therapist or patient to hold the device at a particular range from the area of skin requiring treatment for many minutes at a time. For example, the handheld wand may be required to be held just above a treatment site for anywhere from 15 seconds to 1 hour. Therapists and patients find it difficult to hold the device in place for such long periods of time. This problem is particularly exacerbated in patients with severe pain or chronic neuropathy, in situations where the device needs to be proximate to the skin, but not touching the skin due to pain, and in situations where the patient is attempting to self-treat but the location of the pain is difficult to reach.

It is therefore desirable to have a system for transforming a conventionally handheld treatment method into a hands-free treatment method. It is further desirable to have a way of securing a cold laser wand to any portion of the patient's body, thereby enabling hands-free treatment in difficult to reach locations. It is further desirable to have a securing system that can accommodate different size wands to enable a clinician to use different therapeutic modalities. It is also desirable to have a securing system that can adjust the distance of the wand head from the patient's skin to allow for a range of different exposure distances and to better capture and direct light from a device to the patient's skin.

Referring to FIG. 1, a handheld wand and attachment system 100 are shown. The exemplary handheld wand 115 is shown comprising a body 120 having a light generator incorporated therein or an optical light transmission system that receives light from an external light generator and transmits it to the light emission surface 130. The light emission surface 130 is defined by a periphery 135 that circumscribes the light emission surface 130 which has a plurality of light emitting diodes or optical fiber emission points responsible for the actual emission of light.

Separate from the wand 115 is a holder system comprising a light emission surface receiver 110 connected, using a connection means 105, to an attachment surface 103. The light emission surface receiver 110 may have a fixed circumference, size, or periphery configured to securely, and internally, receive the periphery 135 of the light emission surface 130. The light emission surface receiver 110 comprises a hollow cavity, defined by a peripheral wall 140. The internal surface of light emission surface receiver 110 may be securely attached to the external periphery 135 of the light emission surface 130 through a friction fit, snap fit, the mating of a groove with a protrusion, Velcro, snaps, or other connection mechanism, the components of which may be located on either the external periphery of the light emission surface 130 and/or the internal periphery of the light emission surface receiver 110.

Figure 5:
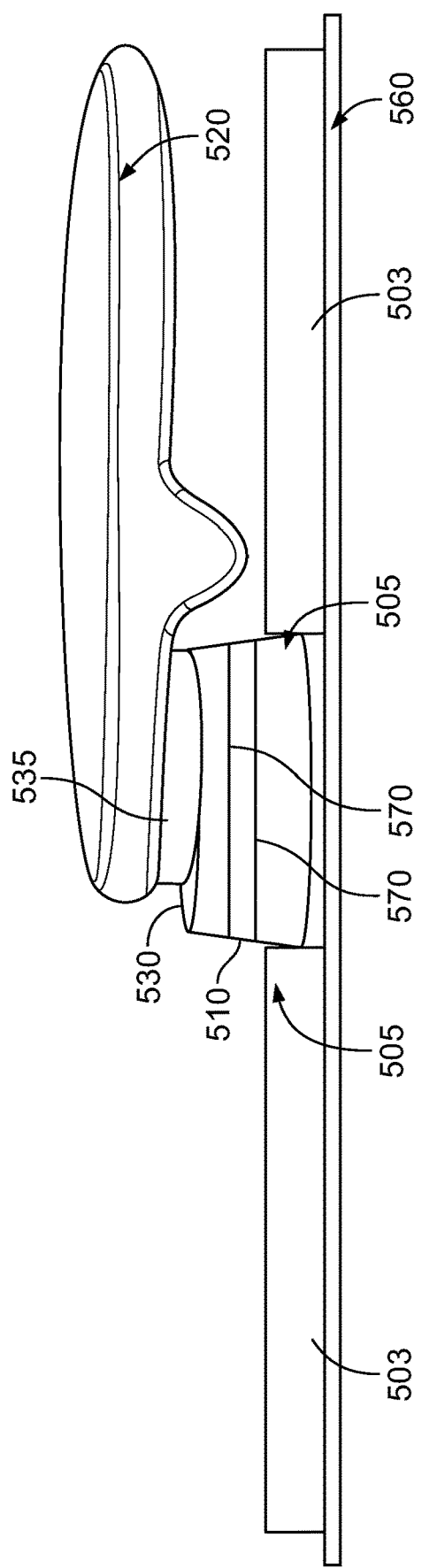
FIG. 5 illustrates a telescopic light emission surface that may receive and position a handheld wand at different distances from the patient's skin, in accordance with some embodiments of the present specification.

Alternatively, the light emission surface receiver 110 may have an adjustable circumference, size, or periphery configured to be adjusted in order to adapt to the size of the periphery of the light emission surface 130 and thereby securely receive the periphery 135. The circumference, size or periphery may be adjusted by having a telescoping structure that, when pulled upwards, releases smaller and smaller peripheries until the right size is achieved, as shown in FIG. 5 by elements 570. The circumference, size or periphery may be adjusted by having a rotatable portion, attached to the periphery of the light emission receiver 110 that, when rotated, causes the periphery of the light emission receiver 110 to decrease or increase in size, thereby enabling the size of the periphery to be adjusted.

In some embodiments, internal surface of the wall of receiver 110 comprises a reflective material that is positioned to cause light emitted from the light emission surface 130 and impinging on the internal surface of the wall of receiver 110 to be directed toward the patient's skin. In some embodiments, at least 5% of the internal surface of the wall comprises the reflective material. In some embodiments, at least 50% of the internal surface of the wall comprises the reflective material. In some embodiments, at least 95% of the internal surface of the wall comprises the reflective material. The internal surface of the wall may comprise reflective material on 1% to 99%, or any increment therein, of the surface area.

The light emission surface 130 and corresponding receiver 110 may adopt a plurality of different shapes. FIGS. 2A to 2J illustrate multiple embodiments of wand 115 with light emission surfaces 130 of different shapes and sizes, in accordance with the present specification. Additionally, FIGS. 3A to 3J illustrate top views of multiple embodiments of light emission receivers 110 of different shapes and sizes that geometrically, or shape-wise, correspond to the embodiments illustrated in FIGS. 2A to 2J.

Figure 3A:
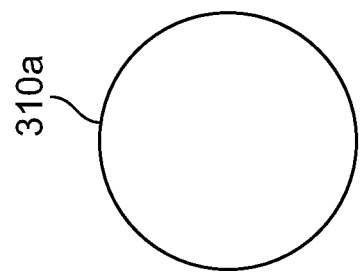
FIG. 3A illustrates a top view of a first embodiment of a light emission receiver, incorporated into a patient attachment system, of a first shape and first size that corresponds to the embodiment illustrated in FIG. 2A.
Figure 2A:
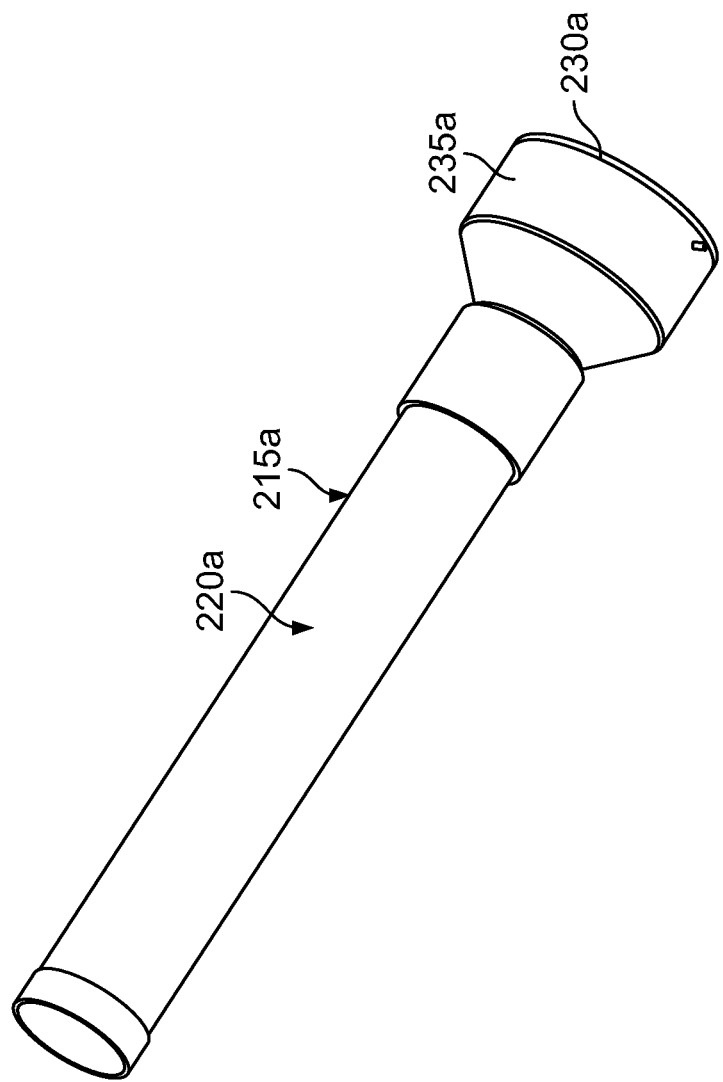
FIG. 2A illustrates a first embodiment of a wand with light emission surfaces of a first shape and a first size, in accordance with the present specification.

Referring simultaneously to FIGS. 2A and 3A, an exemplary handheld wand 215a is shown comprising a body 220a having a light emission surface 230a. The light emission surface 230a is defined by a periphery 235a that circumscribes the light emission surface 230a which has a plurality of light emitting diodes or optical fiber emission points responsible for the actual emission of light. In this embodiment, wand 215a has an elongated cylindrical body 220a for ease of holding and handling. One end of the elongated cylindrical body comprises a light generator incorporated therein or is attached to an optical light transmission system that receives light from an external light generator and transmits it to light emission surface 230a that is circular in shape. In embodiments light emission surface 230a has a larger diameter than that of the elongated cylindrical body of wand 215a, such that wand 215a appears in the shape of a torch. Corresponding light emission surface receiver 310a is circular with a circumferential shape that matches that of light emission surface 230a but is slightly larger to receive the light emission surface receiver 310a.

In embodiments, light emission surface receiver 310a is connected, using a connection means, to an attachment surface. The attachment surface may be used to attach holder comprising receiver 310a that fixedly holds light emission surface 230a over a patient's skin surface. The light emission surface receiver 310a may have a fixed circumference, size, or periphery configured to securely receive the periphery 235a of the light emission surface 230a. Light emission surface receiver 310a comprises a hollow cavity, defined by a peripheral wall. The internal surface of light emission surface receiver 310a may be securely attached to the external periphery of the light emission surface 230a through a friction fit, snap fit, the mating of a groove with a protrusion, Velcro, snaps, or other connection mechanism, the components of which may be located on either the external periphery of the light emission surface 230a or the internal periphery of light emission surface receiver 310a.

In some embodiments, in accordance with the present specification, wall of light emission surface receiver 110, 310a, or any other exemplary embodiment described herein, is configured to be porous in order to allow heat generated by light emitted from light emission surface 130 (230a, or any other similar light emission surface described herein) to escape. FIGS. 4A to 4D illustrates views of an exemplary embodiment of a wall of light emission surface receiver 410 configured with spaces, voids, pores, or openings 440 that are spread evenly on the surface of light emission surface receiver 410. In various embodiments, the openings 440 may be of different shapes and sizes and may be configured in different patterns as a single pore or multiple pores on the surface of wall of light emission surface receiver 410. FIG. 4A illustrates a front view of the exemplary embodiment of wall of light emission surface receiver 410 configured with spaces, voids, pores, or openings 440 that are spread evenly on the surface of light emission surface receiver 410.

Figure 4C:
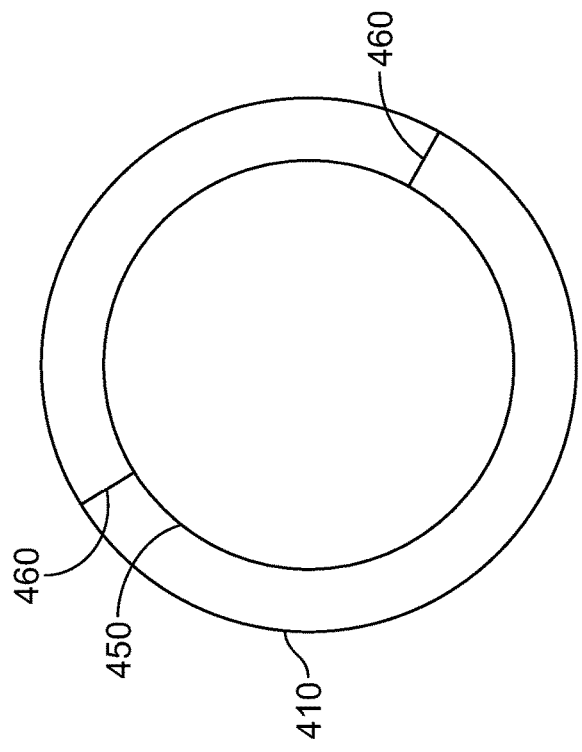
FIG. 4C illustrates a top view of an inner wall of a light emission surface receiver, in accordance with some embodiments of the present specification.
Figure 4D:
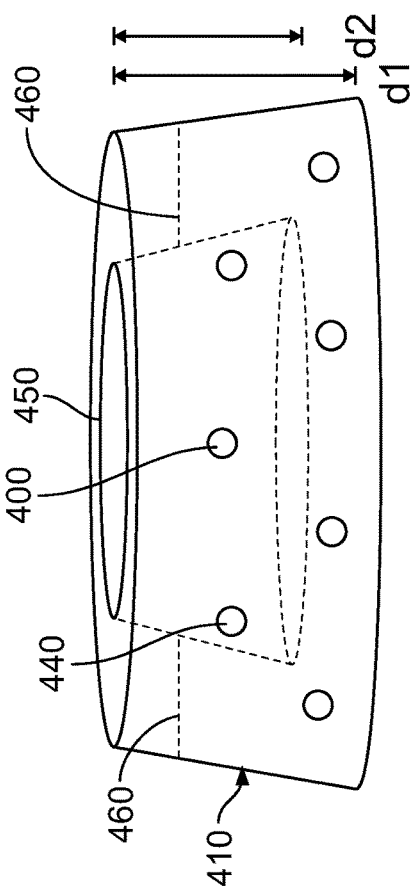
FIG. 4D illustrates a see-through front view of a wall of a light emission surface receiver configured with spaces, voids, pores, or openings that are spread evenly on the surface of light emission surface receiver and an inner wall, in accordance with some embodiments of the present specification.
Figure 4A:
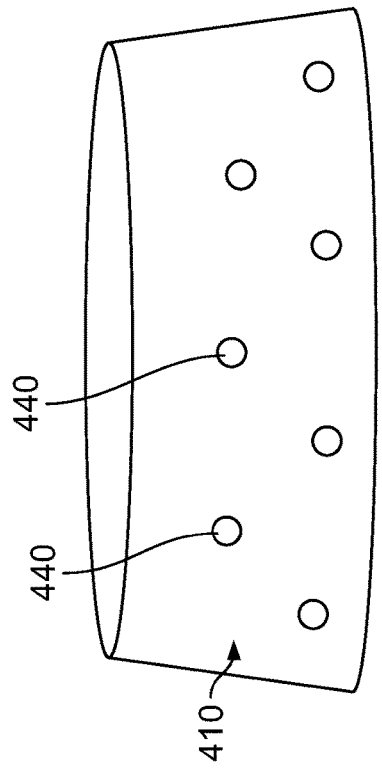
FIG. 4A illustrates a front view of a wall of a light emission surface receiver configured with spaces, voids, pores, or openings that are spread evenly on the surface of light emission surface receiver, in accordance with some embodiments of the present specification.
Figure 4B:
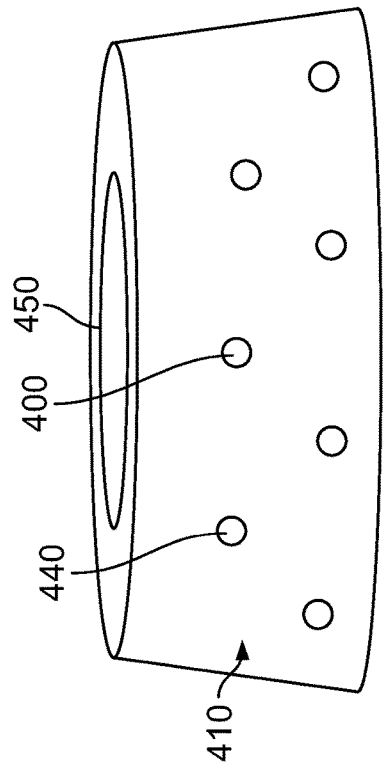
FIG. 4B illustrates a front view of a wall of a light emission surface receiver configured with spaces, voids, pores, or openings that are spread evenly on the surface of light emission surface receiver and an inner wall, in accordance with some embodiments of the present specification.

In another embodiment, illustrated in FIG. 4B, in order to capture and direct light but still allow heat to escape, the light emission surface receiver 410 may comprise an internal wall 450 that is configured to physically receive, and attach to, the light emission surface of the wand, as previously described above. The internal wall 450 may have the same characteristics as described above with respect to the light emission surface receiver, such as a telescoping structure and/or reflective surface on the interior surface of the internal wall. The external surface of the internal wall 450 is attached to the interior surface of the external wall 410 at one or more points through one or more linear members 460, as shown in the top view of FIG. 4C. In such an embodiment, the internal wall 450 functions as the light emission surface receiver 410 while the external wall 410 comprises openings 440 that allow heat to escape.

Figure 3C:
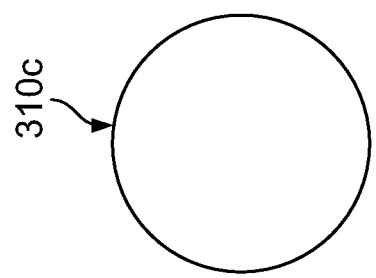
FIG. 3C illustrates a top view of a third embodiment of a light emission receiver, incorporated into a patient attachment system, of a third shape and third size that corresponds to the embodiment illustrated in FIG. 2C.

Referring to FIG. 4D, to permit the flow of heat, preferably the length of the external wall 410, measured as the distance from the base of the external wall 410 (which attaches to the patient attachment surface) to the top of the external wall 410 (which is proximate the light emission surface of the wand) and referred to as d1, is greater than the corresponding length of the internal wall 450, referred to as d2. Generated heat flows out from within the cavity defined by the interior surface of the internal wall 450, patient skin, and light emission surface, into the cavity defined by the exterior surface of the internal wall 450, interior surface of the external wall 410 and patient skin, and out through the openings 460 or the space between the top of the external wall 410 and wand and/or internal wall 450. It should be appreciated that the embodiments depicted in FIGS. 4A to 4D may be used with any of the wand configurations shown in FIGS. 2A to 2J and corresponding FIGS. 3A to 3J.

Referring simultaneously to FIGS. 2B and 3B, an exemplary handheld wand 215b is shown comprising a body 220b having a light emission surface 230b. The light emission surface 230b is defined by a periphery 235b that circumscribes light emission surface 230b which has a plurality of light emitting diodes or optical fiber emission points 240b responsible for the actual emission of light. In this embodiment, wand 215b has an elongated oval body 220b for ease of holding and handling. One end of the elongated cylindrical body comprises a light generator incorporated therein or is in optical communication with an optical light transmission system that receives light from an external light generator and transmits it to light emission surface 230b that is circular in shape. In embodiments, light emission surface 230b has a diameter that lies within the oval-shaped edge of body of wand 215b. In embodiments, body 220b comprises a smooth pyramidal protrusion 245b that extends on a portion of it surface between one end of body 220b comprising light emission surface 230b and the other end. Protrusion 245b may be configured to support and stabilize position on wand 215b when it is placed over a holder, by allowing protrusion 245b to rest over the patient's skin surface or over an attachment surface in order to maintain light emission surface 230b in a parallel orientation to the patient's skin surface. Further, wand 215b comprises a corresponding light emission surface receiver 310b that is circular with a circumference to match that of light emission surface 230b.

In embodiments, light emission surface receiver 310b is connected, using a connection means, to an attachment surface. The attachment surface may be used to attach holder that fixedly holds light emission surface 230a over a patient's skin surface. The light emission surface receiver 310b may have a fixed circumference, size, or periphery configured to securely receive the periphery 235b of the light emission surface 230b. Light emission surface receiver 310b comprises a hollow cavity, defined by a peripheral wall. The internal surface of light emission surface receiver 310b may be securely attached to the external periphery of the light emission surface 230b through a friction fit, snap fit, the mating of a groove with a protrusion, Velcro, snaps, or other connection mechanism, the components of which may be located on either the external periphery of the light emission surface 230b or the internal periphery of light emission surface receiver 310b.

Figure 2C:
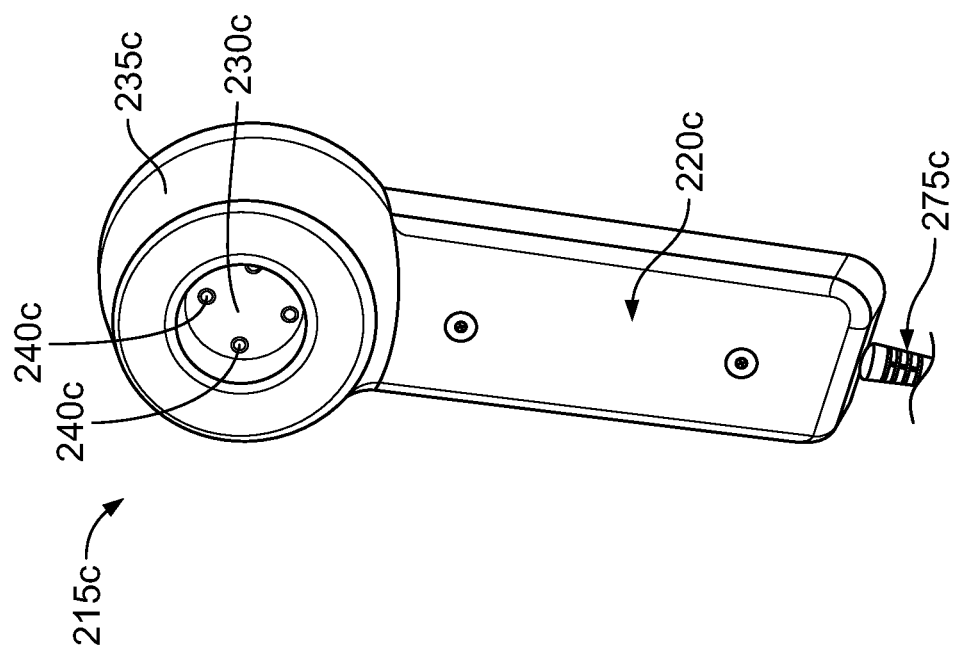
FIG. 2C illustrates a third embodiment of a wand with light emission surfaces of a third shape and a third size, in accordance with the present specification.
Figure 3E:
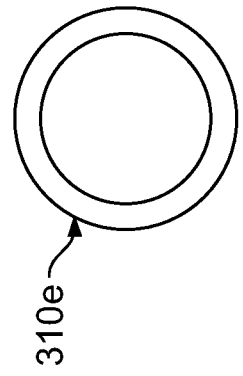
FIG. 3E illustrates a top view of a fifth embodiment of a light emission receiver, incorporated into a patient attachment system, of a fifth shape and fifth size that corresponds to the embodiment illustrated in FIG. 2E.

Referring simultaneously to FIGS. 2C and 3C, an exemplary handheld wand 215c is shown comprising a body 220c having a light emission surface 230c. The light emission surface 230c is defined by a thick periphery 235c that circumscribes light emission surface 230c which has a plurality of light emitting diodes or optical fiber emission points 240c responsible for the actual emission of light. The wand 215c is attached, via cable 275c, to a light generator. In this embodiment, the light emission surface 230c is inset or indented relative to the thick periphery 235c wand 215c. Accordingly, to attach to the light emission surface 230c, the light emission surface receiver 310c may be configured to fit within periphery 235c, such that the internal surface of periphery 235c circumscribes or surrounds the external surface of the light emission receivers 310c.

Light emission surface receiver 310c is connected, using a connection means, to an attachment surface. The attachment surface may be used to attach holder that fixedly holds light emission surface 230c over a patient's skin surface. The light emission surface receiver 310c may have a fixed circumference, size, or periphery configured to securely receive the periphery 235c of the light emission surface 230c. Light emission surface receiver 310c comprises a hollow cavity, defined by a peripheral wall. The external surface of light emission surface receiver 310c may be securely attached to the internal periphery of the light emission surface periphery 235c through a friction fit, snap fit, the mating of a groove with a protrusion, Velcro, snaps, or other connection mechanism, the components of which may be located on either the external periphery of the light emission surface receiver 310c or the internal surface of the periphery of light emission surface 235c.

In the various embodiments of the present specification, internal surfaces of the light emission surface receiver may be covered by a reflective material in areas other than the light emitting diodes or optical fiber emission points. The reflective surface is useful to reflect the light and therefore optimize its effect on a target.

Referring simultaneously to FIGS. 2D and 3D, an exemplary handheld wand 215d is shown comprising a body 220d having a light emission surface 230d and a conical periphery 235d that circumscribes light emission surface 230d. Button 280d may be toggled to turn on and off the light. In this embodiment, wand 215d has an elongated narrow cylindrical body 220d for ease of holding and handling. As in the prior embodiments, the elongated body 220d comprises a light generator incorporated therein or is in electrical communication with an optical light transmission system that receives light from an external light generator and transmits it to light emission surface 230d. Further, wand 215d comprises a corresponding light emission surface receiver 310d that is circular with a circumference to match that of light emission surface 230d. In one embodiment the light emission surface receiver 310d may be conically configured to receive the light emission surface, where the narrow circumferential portion of the conical light emission surface receiver is closer to the patient and the wider circumferential portion of the conical light emission surface receiver is closer to the handheld wand. Grooves 248d on the exterior surface of the periphery 235d light emission surface 230d are configured to mate with protrusions 358d positioned internal to the light emission surface receiver 310d, thereby securing the light emission surface 230d to the light emission surface receiver 310d. It should be appreciated that the grooves could be positioned within the internal surface of the light emission surface receiver 310d and the protrusions could be positioned on the external surface of the periphery 235d. All other features described with respect to other embodiments may equally apply to this geometric configuration.

Figure 2E:
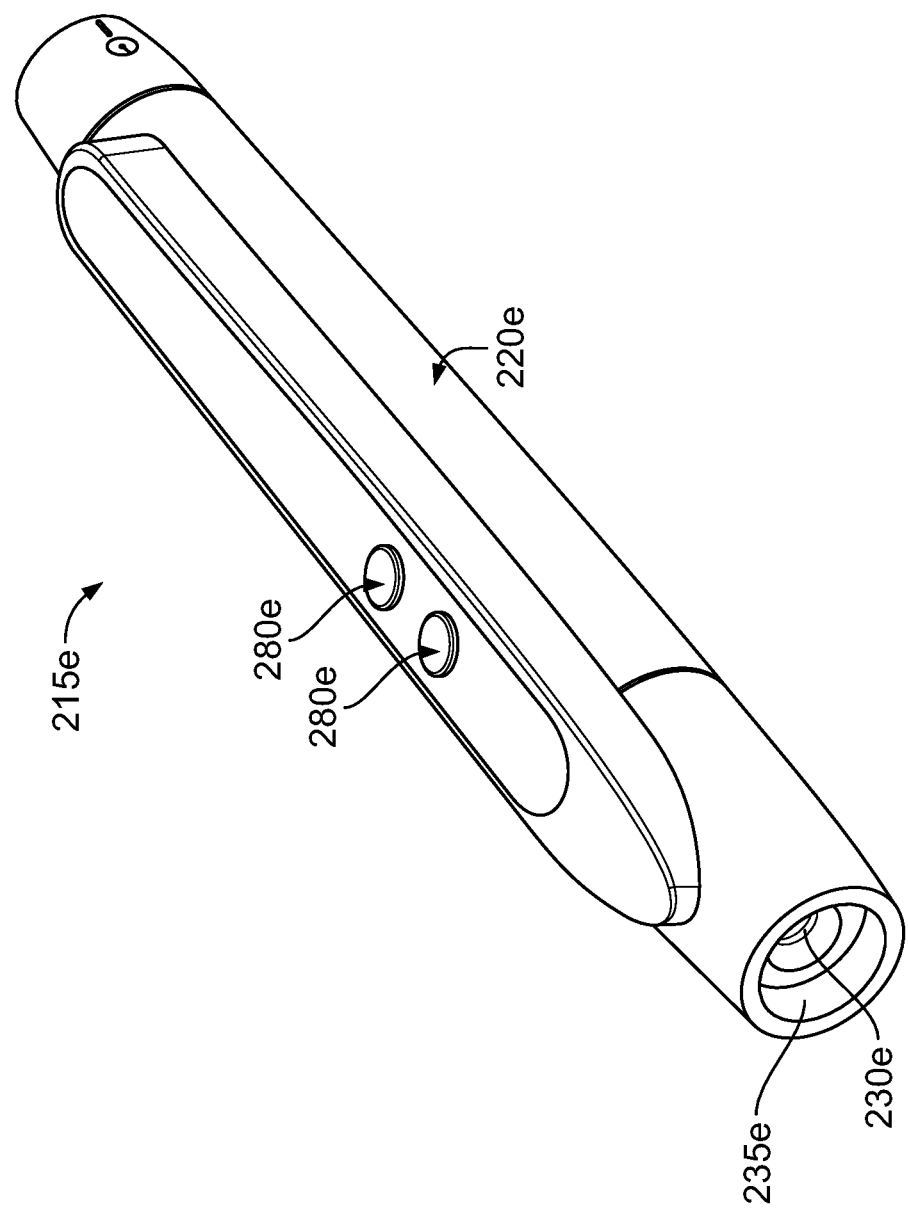
FIG. 2E illustrates a fifth embodiment of a wand with light emission surfaces of a fifth shape and a fifth size, in accordance with the present specification.

Referring simultaneously to FIGS. 2E and 3E, an exemplary handheld wand 215e is shown comprising a body 220e having a light emission surface 230e. The light emission surface 230e is defined by a periphery 235e that circumscribes light emission surface 230e and extends around and ahead of light emission surface 230e such that the light emission surface 230e in indented or inset into the wand 215e. Buttons 280e may be toggled to turn the light on and off, set a time for treatment, or set a preferred light amplitude or intensity. Light emission surface 230e has a plurality of light emitting diodes or optical fiber emission points responsible for the actual emission of light. One end of body 220e comprises a light generator incorporated therein or is in optical communication with an optical light transmission system that receives light from an external light generator and transmits it to light emission surface 230d.

In embodiments, light emission surface 230e is positioned at a flat edge of cylindrical body 220e and has a diameter that is less than a diameter of the flat circular end of elongated cylindrical body of wand 215e. Further, wand 215c comprises a corresponding light emission surface receiver 310c that is circular with a circumference to match that of light emission surface 230c such that it may either friction fit around or within external periphery 235e. All other features described with respect to other embodiments may equally apply to this geometric configuration.

Referring simultaneously to FIGS. 2F and 3F, an exemplary handheld wand 215f is shown having a light emission surface 230f. The light emission surface 230f is defined by a peripheral wall 235f that circumscribes light emission surface 230f which has a plurality of light emitting diodes or optical fiber emission points 240f responsible for the actual emission of light. In this embodiment, wand 215f has multiple portions attached to each other. A cylindrical body 220f has two ends—a distal end 221f and a proximal end 222*f*, which are respectively distal and proximal to light emission surface 230*f*. In some embodiments, each end 221*f* and 222*f* has a conical structure with a side connected to body 220*f* having a larger diameter compared to the other side away from body 220*f* having a relatively smaller diameter. In embodiments, the side with the larger diameter has a circumference equal to cylindrical body 220*f*. The side with smaller diameter of end 221*f* may be connected further to a cable encompassing electrical and/or optical components that enable lighting of points 240*f*. The side with small diameter of end 222*f* may be connected to a circular surface of another cylindrical structure 242*f* One end of structure 242*f* may be attached to another cylindrical structure 235*f* of a diameter that is relatively larger than that of structure 242*f*, where structure 235*f* forms periphery to light emission surface 230*f* The corresponding light emission surface receiver 310*f* is circular with a circumference to match that of light emission surface 230*f*. All other features described with respect to other embodiments may equally apply to this geometric configuration.

Referring simultaneously to FIGS. 2G and 3G, an exemplary handheld wand 215*g* is shown comprising a body 220*g* having a light emission surface 230*g*. The light emission surface 230*g* is defined by a periphery 235*g* that circumscribes light emission surface 230*g* which has one or more light emitting diodes or optical fiber emission points responsible for the actual emission of light. In this embodiment, wand 215*g* comprises a cylindrical body 220*g*. A distal end of the cylindrical body 221*g* is connected to a cable that may comprise electrical and/or optical components to power emission of light from light emission surface 230*g*. A proximal end of the cylindrical body 220*g* is connected to another cylindrical structure 231*g* extending in the longitudinal direction of body 220*g* and having a smaller diameter than cylindrical body 220*g*. A further conical structure 232*g* may extend from a proximal portion of structure 231*g*. The conical structure may reduce in diameter from its distal end connected to structure 231*g* towards its proximal end, where the proximal end is further connected to another cylindrical structure 233*g* extending in the longitudinal direction of body 220*g* and having a diameter lesser that the smaller proximal end of conical structure 232*g*. Proximal end of the cylindrical structure 233*g* narrows further into a conical shape 234*g* that has a proximal end comprising light emission surface 230*g*. Therefore, the proximal end of body 220*g* comprises a plurality of conical portions that decrease in width as it reaches its light emission surface 230*g*. In some embodiments, a combination of structures 233*g* and 234*g* form the periphery 235*g* for light emission surface 230*h*. Light emission surface receiver 310*g* comprises a conical circumference configured to compliment the shape of conical portions 234*g*, 233*g*, 232*g*, and/or 231*g* to thereby permit the receiving of, and attachment to, the light emission surface. All other features described with respect to other embodiments may equally apply to this geometric configuration.

Referring simultaneously to FIGS. 2H and 3H, an exemplary handheld wand 215*h* is shown comprising a body 220*h* similar to body 220*g* of FIG. 2G. The embodiment illustrated in FIG. 2H is similar to the embodiment of FIG. 2G, except that FIG. 2H illustrates a wand that does not include proximal structures 233*g* and 234*g* at a proximal end of structure 232*h* similar to structure 232*g*. Light emission surface 230*h* is positioned within the proximal end of structure 232*h*. Therefore, a combination of structures 232*h* and 231*h* form a periphery 235*h* for light emission surface 230*h*. The corresponding light emission surface receiver 310*h* is circular or conical with an internal periphery to match that of the external periphery of the light emission surface 230*h*. All other features described with respect to other embodiments may equally apply to this geometric configuration.

Referring simultaneously to FIGS. 2I, 3I, 2J and 3J, an exemplary handheld wand 215*i*, 215*j* is shown comprising a body 220*i*, 220*j*, a rectangular 235*i* or oval 235*j* periphery of a light emission surface, and a light emission surface that is rectangular 230*i* or comprising a plurality of protruding emission structures 235*j*. The corresponding light emission surface receiver is rectangular 310*i* or oval/conical 310*j* with an internal periphery to match that of the external periphery of the light emission surfaces 230*i*, 230*j*. All other features described with respect to other embodiments may equally apply to this geometric configuration.

Referring now to FIG. 5, a light emission surface 530 may be positioned at different distances from the patient's skin 560 by modifying the telescopic structure 570 of the light emission receiver 510. While the figures illustrate an embodiment of a light emitting and receiving system similar to that illustrated in FIG. 1, the positions of all the other embodiments described herein may be varied similarly. Wand 520 having a light emission surface 530 surrounded by a peripheral wall 535 is inserted into light emission receiver 510 that is attached to a patient attachment surface 503 at attachment or connection points 505. The periphery wall of light emission surface receiver 510 may have an adjustable circumference, size, or periphery configured to be adjusted in order to adapt to the distance of the periphery of light emission surface 530 and thereby securely receive the periphery 535. The circumference, size or periphery of receiver 510 may be adjusted by having a telescoping structure that, when pulled upwards, releases smaller and smaller peripheries until the right size and the right distance is achieved. The circumference, size or periphery of receiver 510 may be adjusted by having a rotatable portion, attached to the periphery of the light emission receiver 110 that, when rotated, causes the periphery of the light emission receiver 110 to move up or down, thereby enabling the distance of patient's skin surface from periphery 535 to be adjusted.

In embodiments, light emission surface receiver 510 may be fixedly or removably attached to a patient attachment surface 503. The patient attachment surface 503 may comprise Lycra, spandex, plastic, straps, brace, sleeve, or any flexible material that may be contoured to securely and comfortably attach to a patient. Light emission surface receiver 510 may be attached to patient attachment surface 503 using any connection mechanism, including sewing, gluing, Velcro, snaps, zippers, a friction fit, or the mating of a groove with a protrusion, the components of which may be located on either patient attachment surface 503 or light emission surface receiver 510.

Figure 6A:
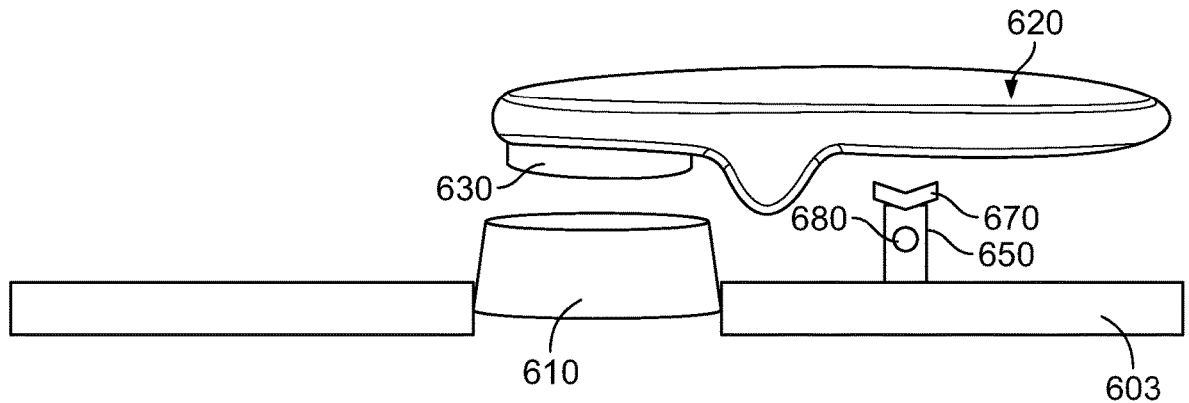
FIG. 6A illustrates a support structure configured to position a body of a wand above a patient's skin surface, in accordance with an embodiment of the present specification.
Figure 6B:
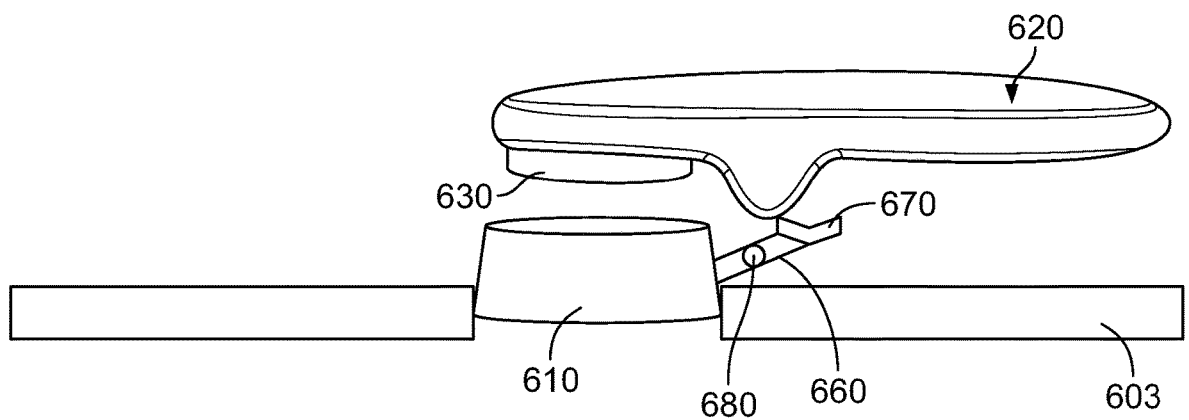
FIG. 6B illustrates a support structure configured to position a body of a wand above a patient's skin surface, in accordance with another embodiment of the present specification.

FIGS. 6A and 6B illustrate embodiments of different support structures to position a body 620 of a wand parallel to, and above, a patient's skin surface, in accordance with some embodiments of the present specification. While the figures illustrate two types of support structures 650 and 660, other types of support structures that can hold up body 620 of the wand and keep it parallel to the attachment surface, are possible. Support structures 650 and 660 may be adjustable, rotatable, or otherwise movable so that the body of the wand can be held up and kept parallel to the attachment surface, thereby making sure light emission surface 630 does not tilt when inserted into, and left within, the light emission surface receiver 610. Therefore, in some embodiments, wand body support structure 650/660 is attached to at least one of light emission surface receiver 610 or the patient attachment surface 603 through a hinge mechanism that allows rotation of the support structure 650/660 around the hinge joint.

Referring to FIG. 6A, wand body support structure 650 connected to an inner surface of body 620 of a wand extends and stands perpendicularly on either a patient attachment surface 603, or directly on a patient's skin surface. Preferably, the wand body support structure 650 has a first end and an opposing second end. The wand body support structure 650, attached at the first end to the patient attachment structure 603, may rotate from a position that is substantially parallel, and positioned against, the patient attachment structure 603 to a position that is substantially perpendicular to the patient attachment structure 603. The wand body support structure 650 may also have a wand body receiver 670, attached to the second end, that is padded, flat, or indented, concave or otherwise curved to receive the body of the wand 620. Length adjustment mechanism 680, which may comprise a turn dial that causes a pair of telescoping members to move relative to each other, may be used to adjust the height of the wand body support structure 650.

FIG. 6B illustrates another embodiment of a wand body support structure 660 that extends from an inner surface of body 620 of the wand to an outer surface of light emission surface receiver 610, such that support 660 is positioned diagonally between the wand and patient surface or patient attachment surface. The wand body support structure 660 has a first end and an opposing second end. The wand body support structure 660, attached at the first end to the light emission surface receiver 610, may rotate from a position that is substantially parallel, and positioned against, the patient attachment structure 603 to a position that is substantially diagonal to the patient attachment structure 603. The wand body support structure 660 may also have a wand body receiver 670, attached to the second end, that is padded, flat, or indented, concave or otherwise curved to receive the body of the wand 620. Length adjustment mechanism 680, which may comprise a turn dial that causes a pair of telescoping members to move relative to each other, may be used to adjust the length of the wand body support structure 660.

Figure 7:
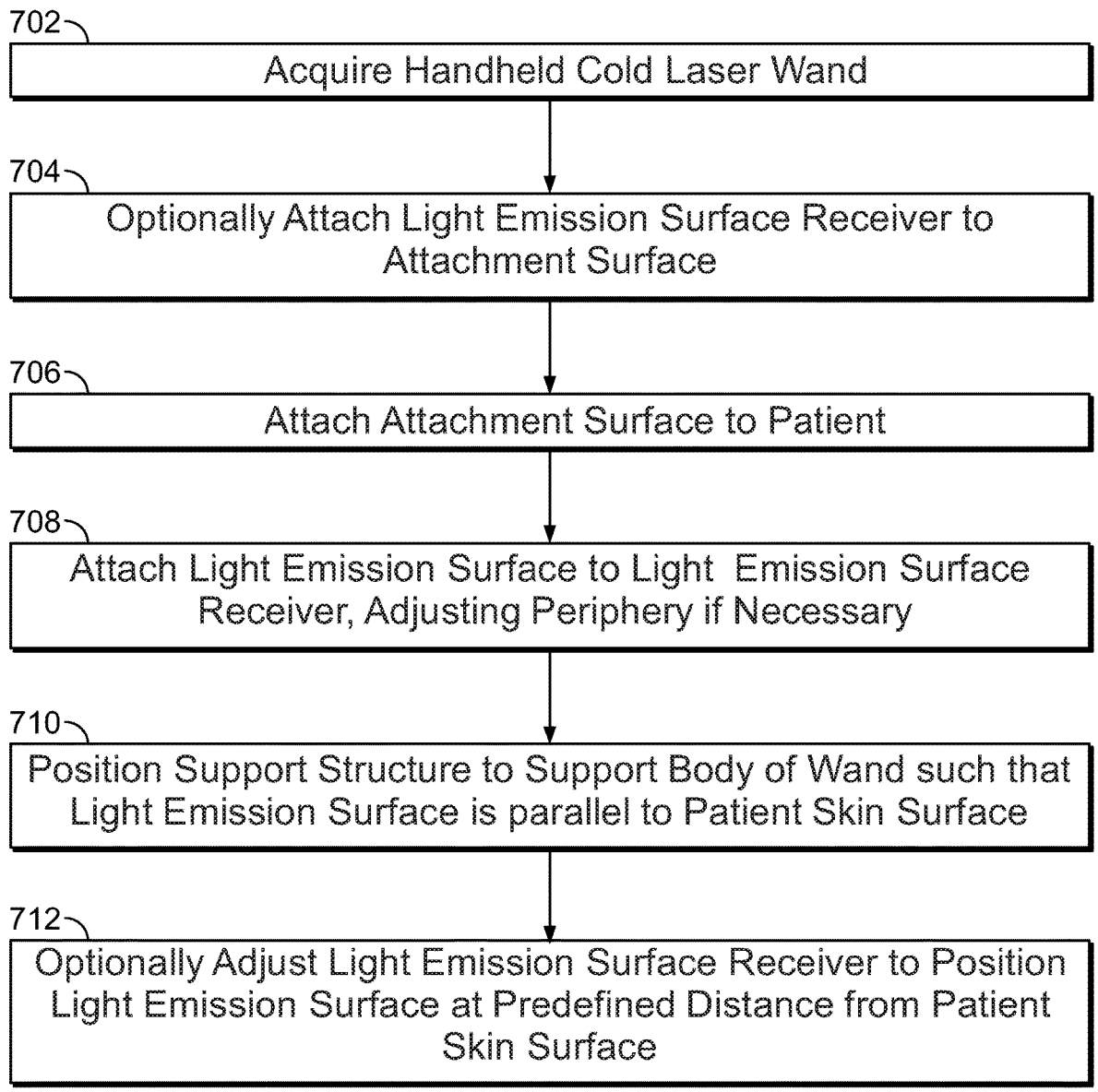
FIG. 7 is a flow chart to illustrate an exemplary process of using a system in accordance with the various embodiments of the present specification.

FIG. 7 is a flow chart illustrating an exemplary method of using a system in accordance with the various embodiments of the present specification. Referring simultaneously to FIGS. 1 and 7, at step 702, a handheld cold laser wand 100 is acquired by a patient, a physician, or any caretaker attending to the patient. At step 704, optionally, a light emission surface receiver 110 is attached to an attachment surface 103. If at step 704 attachment surface 103 is used, then at step 706, attachment surface 103 is attached to the patient. Alternatively, light emission surface receiver 110 is placed on the patient's skin surface where the treatment in accordance with the present specification, is required. At step 708, light emission surface 130 is attached to light emission surface receiver 110. A periphery of light emission surface receiver 110 may be adjusted if necessary to enable a secure attachment between the light emission surface and the receiver and/or to provide for the right distance from the patient's skin to the light emission surface. At step 710, the wand body support member is manipulated to position it to support the body 102 of the wand such that light emission surface 130 is parallel to the surface of the patient's skin. Examples of support structures are illustrated and described in context of FIGS. 6A and 6B. At step 712, light emission surface receiver 110 may be further adjusted to position the light emission surface at a predefined distance from the patient's skin. The distance may be adjusted by the user by pulling the wand 100 towards or away from the patient's skin surface or by adjusting the support structure, if provided, between body 120 of the wand 100 and light emission surface receiver 110 to thereby achieve a distance of 0.1 mm to 5 cm. Preferably distance measurement marks are provided on the external surface of the light emission receiver surface or wand body support structure to provide a user with guidance on the actual distance between the light emission surface and the patient's skin.

Figure 8:
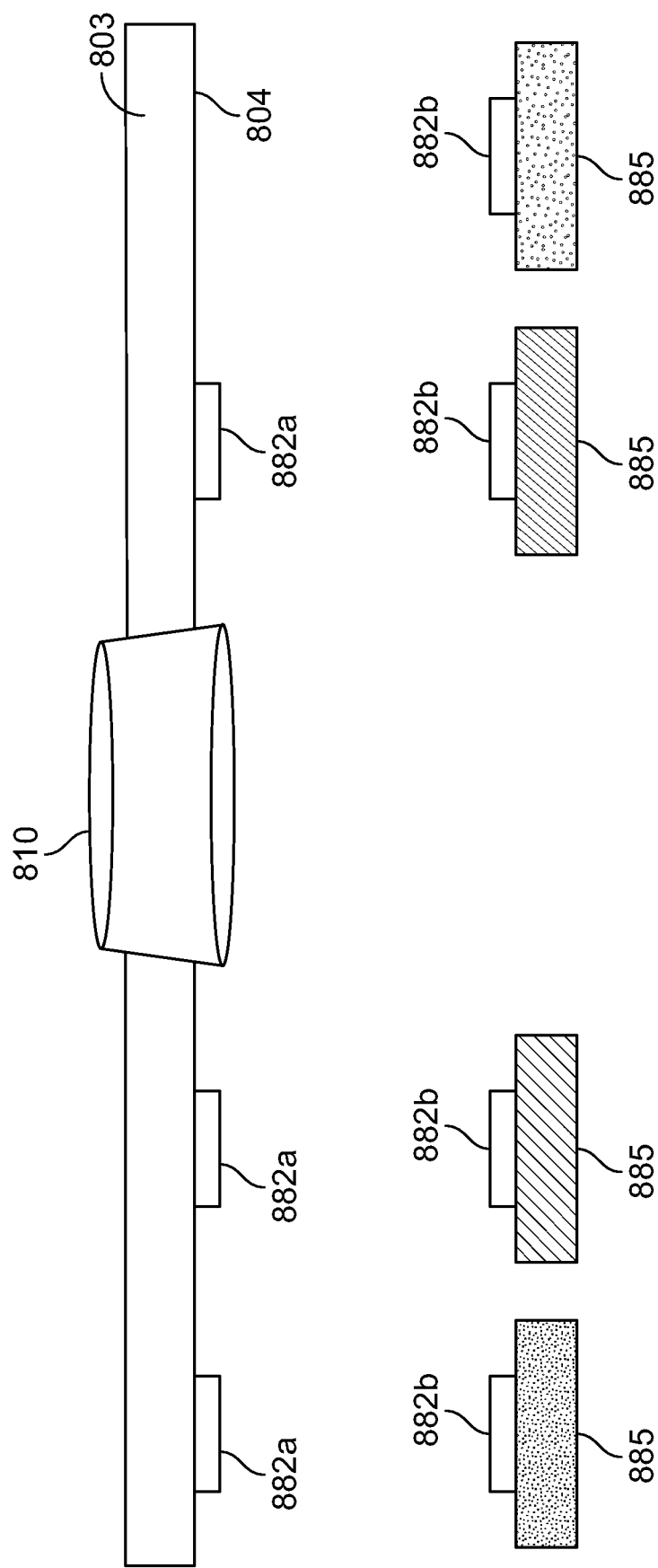
FIG. 8 is an embodiment of the patient attachment device in accordance with an embodiment of the present invention.

Referring to FIG. 8, certain patients may be unable to physically tolerate the feeling or sensation of particular materials, thereby limiting the efficacy of a patient attachment device 803. Accordingly, in one embodiment, the bottom surface 804 of the patient attachment device 803 comprises a plurality of attachment surfaces 882a that comprise connectors, such as Velcro, snaps, pockets, grooves, protrusions or other connection mechanisms. Different materials 885 may then be attached using complementary connectors 882b, such as Velcro, snaps, pockets, grooves, protrusions or other connection mechanisms, depending on what materials are tolerable to the patient. For example, certain patients may only tolerate a silk-based material 885 while others may only tolerate a cotton, wool, velvet, or low durometer polymer (less than shore 40a) material 885. It should be appreciated that, in such a situation, the patient attachment surface 803 may be elevated due to the insertion or inclusion of differential materials having varied thicknesses 885. In such a situation, the light emission surface receiver 810 may be inset relative to the patient attachment device 803, thereby being closer to the patient's skin (although preferably not touching the patient's skin) relative to the plane defined by the bottom surface of the patient attachment device 803. In one embodiment, the light emission surface receiver 810 may be moved perpendicular to the plane defined by the patient attachment surface 803 to thereby insure the light emitted is sufficiently close to the patient's skin but not too close to be painful to the patient.

Figure 9:
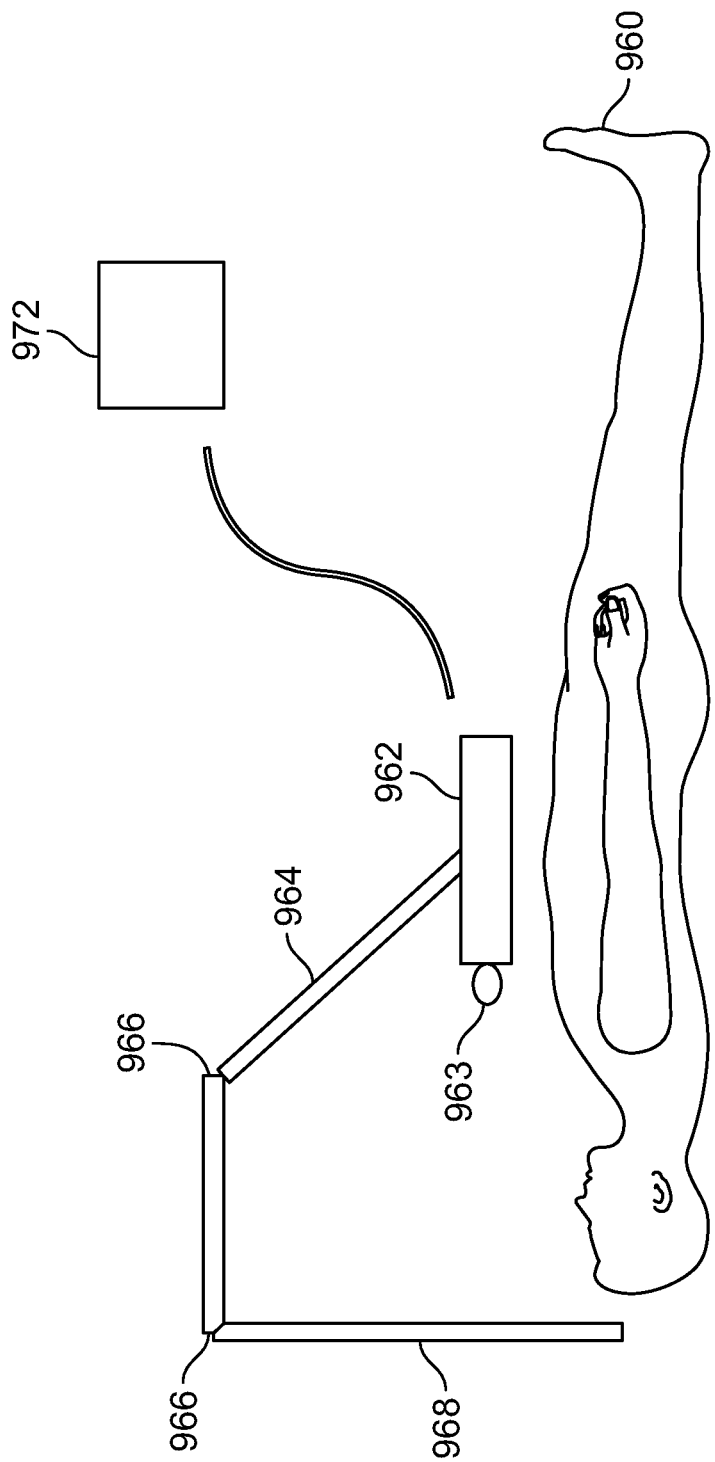
FIG. 9 is an embodiment of a system enabling a programmed application of therapy to a plurality of anatomical locations in an automated, hands-free manner.
Figure 10:
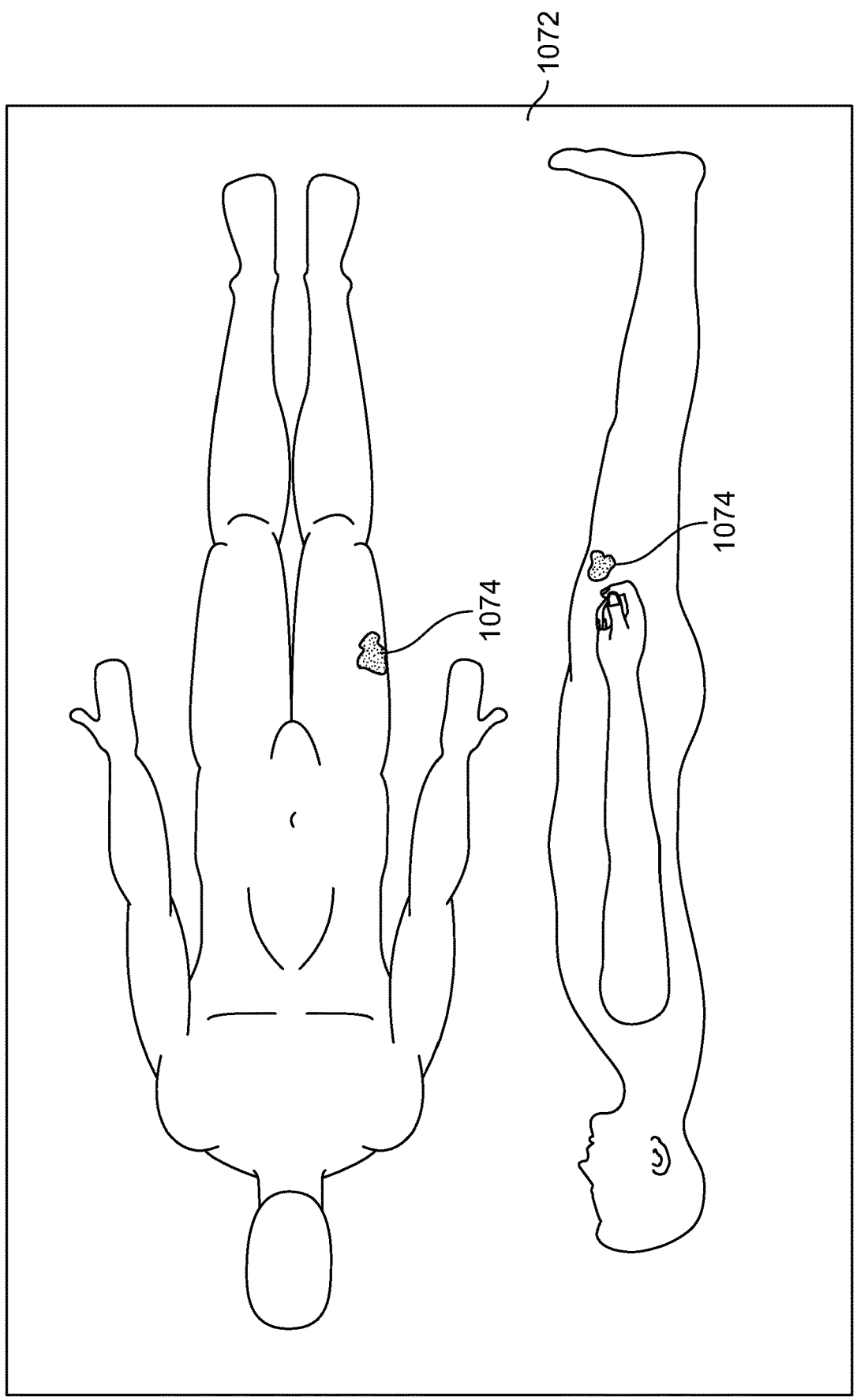
FIG. 10 illustrates an exemplary visual display that is in data communication with the controller of FIG. 9.

FIG. 9 illustrates another approach to the hands-free administration of cold laser therapy, particularly where multiple anatomical sites need to be illuminated during a treatment session. A robotic arm 968 controls the positioning of a light emitting device 962, in accordance with some embodiments of the present specification. Device 962 is held by arm 968, in place of holding it by hand, where arm 968 may also control its position such that device 962 is either fixed or moved in a designated pattern over anatomical locations of a patient 960. In some embodiments, device 962 is a light array, equivalent to the above described light emitting surfaces, that is activated, deactivated, and otherwise controlled based upon instructions from a controller 970 that connects through a wire or wirelessly to device 962. Controller 970 may be programmed by providing a visual display of a human body and selecting areas on the body where pain exists. A camera 963, or mobile phone comprising a camera, may be attached to the arm 968 or device 962 to aid in identifying locations where pain exists in a patient's body and to obtain a visual of the patient's anatomy before and/or during treatment. FIG. 10 illustrates an exemplary visual display 1072 that generates data for a program executing by or within controller 970 to control the positioning of device 962 so as to emit light on the areas that are experiencing pain. The exemplary visual displays a colored mark 1074 indicting pain in the thigh area of the patient in a top view and a side view of anatomy of a patient.

In some embodiments, robotic arm 968 comprises multiple components such as support members 964 that are hinged at one or more locations 966 to control the movement and position of device 962. Once the pain locations are selected, controller 970 translates the selected location of the pain into a plurality of arm 968 positions based on one or more parameters. For example, the selected location of the pain is translated into a plurality of arm 968 positions based on the location of associated nerves, tissues, or other organs that have to be irradiated with light to treat the identified loci of pain.

In some cases, location of the associated nerves, tissues, or other organs may be different from the locations identified in visual display 1072 over the patient's anatomy. In one example, the patient experiencing pain in the thigh may need light therapy in accordance with the present specification, over the lower back. In this example, the visual display and the patient indicate that the pain exists in the thigh. Controller 970 may translate this information to plurality of arm 968 positions that irradiate light over the lower back. A database, table, or memory structure is preferably stored in the controller or remotely accessible by the controller and comprises a plurality of translation data, wherein a selection of a particular anatomical location as having pain, tingling, numb, or other undesired sensation may be translated into a plurality of different anatomical locations requiring illumination by the light emitting device.

Figure 11:
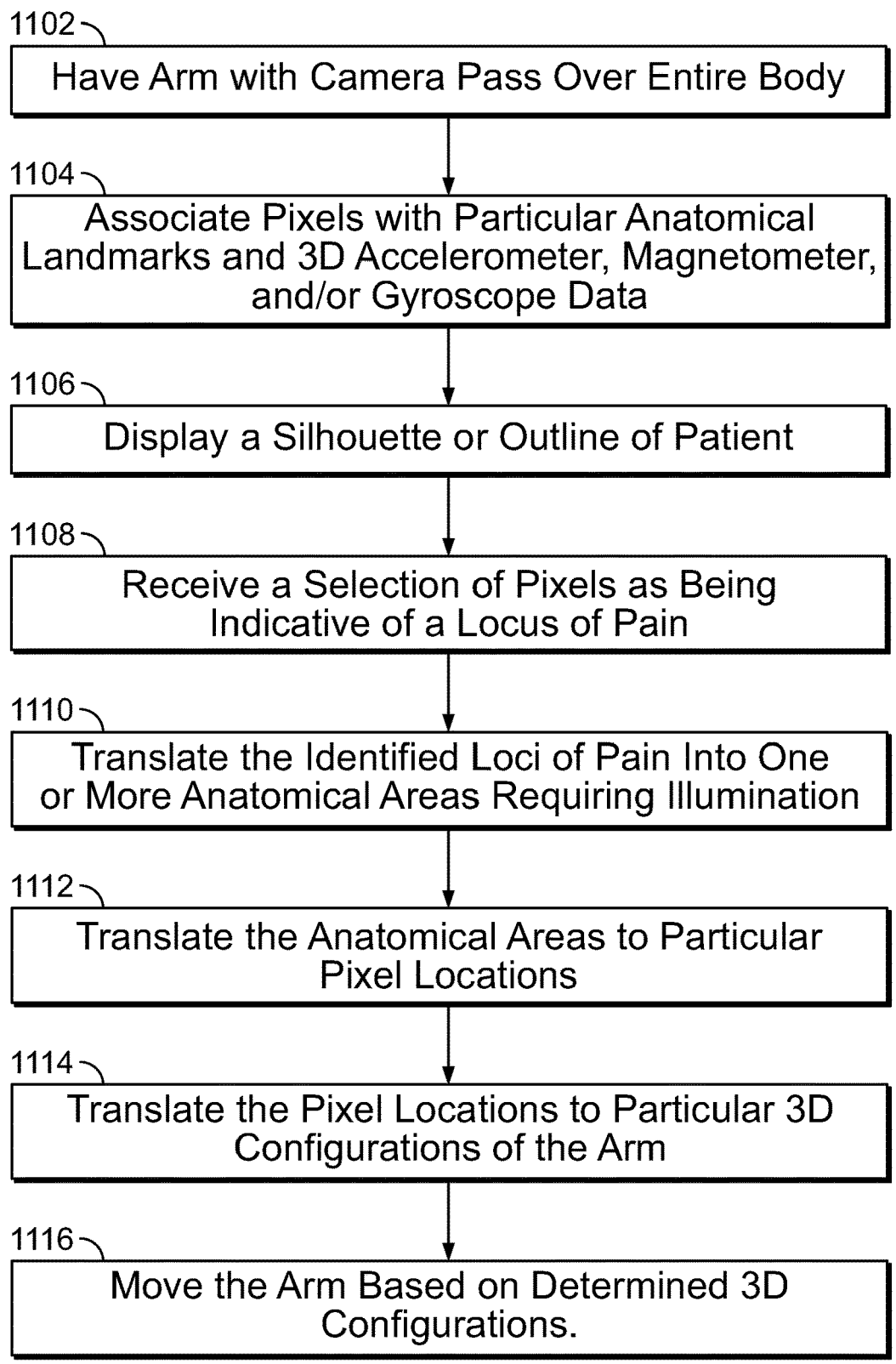
FIG. 11 is a flow chart to illustrate an exemplary process of calibrating and using the system of FIG. 9.

Referring to FIG. 11, in one embodiment, the present invention is directed to a method of treating pain by calibrating a robotic arm, wherein the calibration occurs by attaching a camera, or mobile phone, to a portion of the arm (preferably to the same portion of the arm to which the light array will eventually be attached), having the controller move the arm, and therefore the camera, over the entirety of the patient's body (as the patient lays horizontally, preferably) 1102 and having the controller associate discernable anatomical landmarks (such as shoulders, hands, legs, feet, armpits, head) with pixel values and, in turn, with three dimensional location information, such as accelerometer, magnetometer, and/or gyroscope data that is associated with the captured pixel information 1104. It should be appreciated that the accelerometer, magnetometer, or gyroscope data may be read from the tablet computer or from a set of sensors that may be positioned at the distal end of the robotic arm. Accordingly, controller 970 translates the selected location of the pain into a plurality of arm 968 positions based on a calibration of arm 968 relative to the patient body so that it knows where it is relative to a target tissue. Camera 963 may therefore obtain a visual of the entire body while it associates specific pixels or visual landmarks with particular positions on the patient's body and particular internal accelerometer, gyroscope and/or magnetometer data. Once a particular portion of the anatomical display is selected (to identify loci of pain), controller 970 is able to position arm 968 over the associated physical position and assumes that position in order to expose the loci to light emitting from device 962.

Once the patient's body has been scanned, associated with pixel and 3 dimensional positioning information, the mobile phone or tablet device may be removed from the arm and the light emitting device may be put in its place. The controller, via an integrated display or a remotely connected display on a tablet or phone, will extract a silhouette or some other abstraction of the patient's body (from the captured images) and display it 1106. The patient or physician will then select areas of the body which are in pain and the controller will therefore receive a selection of pixels as being indicative of loci of pain 1108. The controller is configured to translate the identified pixels into anatomical locations, based on the calibration and prior mapping, and further configured to translate those first identified anatomical locations into a second set of anatomical locations, different from the first, based on a translation step as described above 1110. With the selected first set of identified anatomical locations and the translated second set of identified anatomical locations established, a full list of associated pixel locations are determined 1112 and the associated three dimensional configurations of the robotic arm are determined 1114. The system is then initiated to move the arm based on the determined three dimensional configurations 1116.

Controller 970 may be further configured to move the arm in accordance with a predefined set of time periods, based on a required time for irradiation for a given anatomical location. In some cases, the required time for irradiation may be 5 seconds, while at another location the time required may be 10 seconds. Controller 970 may adjust the time of irradiation at each position of arm 968, based on the anatomical location to be illuminated. For example, arm 968 is controlled by controller 970 to move device 962 over different pain locations and irradiate light for similar or different times at each location.

In yet another example, controller 970 translates the selected location of the pain into a plurality of arm 968 positions based on a preferred sequence for irradiating multiple locations over the anatomy of the patient in order to treat pain in a minimal amount of time. For example, suppose patient has identified 3 areas of pain on his back. The controller has translated those three areas of pain into a plurality of anatomical locations requiring illumination, resulting in a total of six areas requiring illumination. The controller then executes a plurality of programmatic instructions to determine the optimum illumination process for delivering a requisite therapeutic dose to the six areas. Such a determination comprises: a) determining a time range for illuminating each of the target locations, b) grouping the target locations based on their proximity to each other (i.e. if two areas are within a predefined distance, such as the width or length of the light emission device, they are grouped together as a single illumination point) and based on each of their determined time ranges (if two areas require different illumination times, they may be treated as different illumination points), and c) determining a sequence of illuminating each of the determined illumination points, which is preferably done serially in one direction along a length of the patient or done based on any medical requirement for one anatomical location to be illuminated prior to, or after, another anatomical location.

In another example, controller 970 translates the selected location of the pain into a plurality of arm 968 positions based on an optimal angle from which the light emitted on a patient's vertical or horizontal body would provide suitable treatment. In one example, a patient experiencing pain on a side of quadriceps muscle of the thigh could lie flat on a table while the controller 970 positions arm 968 at an angle such that device 962 is parallel to a side surface of the thigh.

In some embodiments, device 962 comprises an array of lights where each light, or subset of lights, in the array may be separately controlled by controller 970 to emit for different times or in a sequence, based on an identified position and loci of pain. This may be particularly important where the light emission device has an area sufficient to cover multiple anatomical locations but where each of those anatomical locations require different illumination times, such as anatomical location 1 requiring a longer period of illumination than anatomical location 2. In such a situation, the lights (a first subset of the light array in the light emission device) positioned over anatomical location 2may be turned off after a first period while the lights (a second subset of the light array in the light emission device) positioned over anatomical location 1may be kept on for the entirety of a second period.

While the exemplary embodiments of the present invention are described and illustrated herein, it will be appreciated that they are merely illustrative. It will be understood by those skilled in the art that various changes in form and detail may be made therein without departing from or offending the spirit and scope of the invention.

We claim:

1. A method of treating peripheral neuropathic pain of a patient using an automated photobiomodulation delivery system comprising:
   providing the photobiomodulation delivery system, wherein the photobiomodulation delivery system comprises:
      a light emitting device, wherein the light emitting device is configured to emit light having wavelengths in a range of 600 to 950 nanometers;
      a robotic member, wherein the robotic member is configured to attach to the light emitting device; and
      a controller in data communication with the robotic member;
   attaching a mobile device comprising a camera to the robotic member;
   using the camera of the mobile device to capture images of the patient's anatomy;
   using a visual display of the mobile device to input data representative of the patient's anatomy to be treated, wherein the controller is configured to receive the data representative of the anatomy to be treated and, based on the data, control a positioning of the light emitting device using the robotic member; and
   positioning the light emitting device to deliver light to the patient's anatomy to be treated by moving the robotic member using the controller based on the indication of the patient's anatomy to be treated, wherein the light emitting device is external to the patient.

2. The method of claim 1, wherein the controller is configured to translate data representative of the anatomy to be treated into a plurality of positions of the robotic member.

3. The method of claim 2, further comprising a data structure having a plurality of translation data, wherein the controller is configured to translate data representative of the anatomy to be treated into the plurality of positions of the robotic member using the plurality of translation data.

4. The method of claim 1, wherein the controller is configured to translate data representative of the anatomy to be treated into a plurality of positions of the robotic member and wherein the plurality of positions of the robotic member would result in the irradiation of nerves or tissues associated with locations of the anatomy to be treated.

5. The method of claim 4, wherein locations of said nerves or tissues are different from the locations of the anatomy to be treated.

6. The method of claim 1, further comprising calibrating the robotic member.

7. The method of claim 6, wherein calibrating the robotic member comprises moving the mobile device over the patient's entire body and causing the controller to associate discernable anatomical landmarks with three dimensional location information.

8. The method of claim 7, wherein the anatomical landmarks comprise at least one of the patient's shoulders, hands, legs, feet, armpits, or head.

9. The method of claim 7, wherein the three dimensional location information is derived from at least one of an accelerometer sensor, a magnetometer sensor, or a gyroscope sensor.

10. The method of claim 9, wherein the accelerometer sensor, the magnetometer sensor, or the gyroscope sensor is positioned on a distal end of the robotic member.

11. The method of claim 7, wherein the anatomical landmarks are associated with pixels.

12. The method of claim 1, further comprising associating specific visual landmarks with particular positions on the patient's body and associated accelerometer, gyroscope, or magnetometer data.

13. The method of claim 1, wherein the controller is configured to move the robotic member in accordance with a predefined set of time periods.

14. The method of claim 1, wherein the controller is further configured to determine a sequence of illuminating a series of anatomical locations based on the anatomy of the patient.

15. The method of claim 1, wherein the controller is further configured to determine a time range for illuminating each location of the patient's anatomy to be treated.

16. The method of claim 1, wherein the controller is further configured to group areas of the patient's anatomy to be treated based on their proximity to each other.

17. The method of claim 1, wherein the controller is further configured to determine a sequence of illuminating each location of the patient's anatomy to be treated based on a medical requirement for one anatomical location to be illuminated prior to, or after, another anatomical location.

18. The method of claim 1, wherein the controller is further configured to determine an optimal angle to emit light on the patient's anatomy to be treated.

19. The method of claim 1, wherein the light emitting device comprises a plurality of lights wherein each light in the plurality of lights is configured to be separately controlled by the controller.

20. The method of claim 19, wherein the controller is configured to activate a subset of the plurality of lights.

* * * * *